United States Patent [19]
Walker et al.

[11] Patent Number: 6,022,363
[45] Date of Patent: Feb. 8, 2000

[54] ROTATABLE DYNAMIC SEAL AND GUIDE FOR A MEDICAL OBSTRUCTION TREATMENT DEVICE SUB-ASSEMBLY COUPLED TO A DRIVE MOTOR UNIT

[75] Inventors: Blair D. Walker, Lake Forest; Scott L. Pool, Laguna Hills, both of Calif.

[73] Assignee: Micro Therapeutics, Inc., Irvine, Calif.

[21] Appl. No.: 09/217,786

[22] Filed: Dec. 21, 1998

[51] Int. Cl.[7] .................................................. A61B 17/00
[52] U.S. Cl. ........................................ 606/159; 606/170
[58] Field of Search ............................... 606/1, 158, 170, 606/180; 604/22

[56] References Cited

U.S. PATENT DOCUMENTS

| | | |
|---|---|---|
| 3,614,953 | 10/1971 | Moss . |
| 4,646,736 | 3/1987 | Auth . |
| 4,771,774 | 9/1988 | Simpson et al. . |
| 4,772,258 | 9/1988 | Marangoni et al. . |
| 4,857,045 | 8/1989 | Rydell . |
| 4,917,085 | 4/1990 | Smith . |
| 4,966,162 | 10/1990 | Wang . |
| 4,979,951 | 12/1990 | Simpson . |
| 5,009,659 | 4/1991 | Hamlin et al. . |
| 5,030,201 | 7/1991 | Palestrant . |
| 5,062,648 | 11/1991 | Gomringer . |
| 5,158,564 | 10/1992 | Schnep-Pesch et al. . |
| 5,195,954 | 3/1993 | Schnep-Pesch et al. . |

(List continued on next page.)

FOREIGN PATENT DOCUMENTS

| | | |
|---|---|---|
| 442795 | 9/1974 | Russian Federation . |

OTHER PUBLICATIONS

Hawkins, I. F. et al., "Mechanical Spiral Embolectomy Catheter", Seminars in Interventional Radiology vol. 2, No. 4, pp. 414–418 (Dec., 1995).

Richie, J. L. et al., "Rotational approaches to atherectomy and thrombectomy", Z. Kardiol. 76:Suppl. 6, 59–65 (1987).

Cragg, Andrew H., "The Thrombolytic Brush", presented at The Second Mid–Atlantic Conference on Angio Access: Establishment and Maintenance of Dialysis and Venous Access, Williamsburg, VA (pp. 162–165 of proceedings (Oct. 1996).

"Cragg Thrombolytic Brush™ Quick Review" brochure 75047 Rev a by Micro Therapeutics, Inc. (1997).

"Cragg Thrombolytic Brush™" brochure 75050 Rev A by Micro Therapeutics, Inc. (1997).

*Primary Examiner*—Michael Buiz
*Assistant Examiner*—William W. Lewis
*Attorney, Agent, or Firm*—Joseph F. Breimayer

[57] ABSTRACT

A miniaturized obstruction treatment device, e.g., a brush, particularly adapted for medical use formed at the distal end of an elongated brush drive shaft having a hollow lumen formed therein for introduction over a guidewire. The brush drive shaft is enclosed in the lumen of an brush delivery catheter, and the brush bristles of the distal brush are adapted to be garaged in a distal end section of the brush delivery catheter lumen. A Y-connector and an brush sub-assembly connector are attached to the proximal end of the brush delivery catheter and form an brush sub-assembly with the brush drive shaft and brush. The Y-connector allows infusion of thrombolytic agents into the brush delivery catheter lumen for emission at the distal end opening thereof adjacent the brush. In use, the brush sub-assembly connector connects the brush sub-assembly with a drive motor unit connector of a drive motor unit. The drive motor unit receives the proximal end of the drive shaft and rotates it to rotate the brush bristles. The brush and brush drive shaft distal section are automatically extended out of the catheter lumen distal end opening when the sub-assembly connector and the drive motor unit connector positively lock together. Simultaneously, a drive hub of the brush drive shaft locks into a drive chuck of a drive motor unit to enable rotation of the drive shaft, and the proximal drive shaft end is seated in a dynamic seal that inhibits infiltration of blood and thrombolytic agent into the drive motor housing.

43 Claims, 13 Drawing Sheets

U.S. PATENT DOCUMENTS

| | | |
|---|---|---|
| 5,243,997 | 9/1993 | Uflacker et al. . |
| 5,330,484 | 7/1994 | Gunther et al. . |
| 5,370,653 | 12/1994 | Cragg . |
| 5,423,799 | 6/1995 | Shiu . |
| 5,490,860 | 2/1996 | Middle et al. . |
| 5,667,490 | 9/1997 | Kieth et al. . |
| 5,674,232 | 10/1997 | Halliburton . |
| 5,681,335 | 10/1997 | Serra et al. . |
| 5,882,329 | 3/1999 | Patterson et al. ........................ 606/159 |

ROTATABLE DYNAMIC SEAL AND GUIDE FOR A MEDICAL OBSTRUCTION TREATMENT DEVICE SUB-ASSEMBLY COUPLED TO A DRIVE MOTOR UNIT

CROSS-REFERENCE TO RELATED APPLICATIONS

Reference is hereby made to commonly assigned, co-pending U.S. patent application Ser. Nos. 09/217,785 filed on even date herewith for MINIATURIZED MEDICAL BRUSH in the names of Richard R. Monetti et al., and 09/217,786 filed on even date herewith for ROTATABLE ATTACHMENT MECHANISM FOR ATTACHING A MEDICAL OBSTRUCTION TREATMENT DEVICE SUB-ASSEMBLY TO A DRIVE MOTOR UNIT in the names of Brian M. Strauss et al.

BACKGROUND OF THE INVENTION

1. Field of the Invention

The present invention relates to the assembly of a drive motor unit with an obstruction treatment device sub-assembly particularly adapted for medical use and more particularly to a rotatable seal mechanism for sealing a drive motor unit from infiltration of blood and thrombolytic agent that backflows through the lumen of a hollow drive shaft inserted into a drive motor lumen and guiding means for guiding guidewires or other elongated medical devices through the drive motor unit lumen.

2. Description of the Background Art

Commonly assigned, U.S. Pat. No. 5,370,653 to Cragg, incorporated herein by reference in its entirety, discloses a thrombectomy system for dissolving a soft fibrinous obstruction, such as a recently formed thrombus, within a patient's vascular system, either in a patent vein or artery or in a vascular implant, e.g. an A/V graft. The thrombectomy system employs rotating brush bristles within the thrombus to separate the fibrin of the thrombus from blood cells while mixing the separated fibrin with a dissolving or thrombolytic agent, e.g. streptokinase or urokinase, that is introduced at the same time into the separated fibrin.

Commonly assigned U.S. Pat. No. 5,681,355 to Serra et al., incorporated herein by reference in its entirety, discloses a hollow lumen, thrombectomy brush and method of fabrication which allows for the brush to be introduced over a previously placed guidewire into a very small blood vessel. The miniaturized brush is provided with an elongated, flexible, rotatable brush or drive shaft adapted to be attached at its proximal end to a drive motor for rotating the shaft. The drive shaft is formed with a proximal elongated section formed of a hollow, thin wall tube having an inner lumen and an outer surface and a distal section. The brush is formed of brush filaments, each having first and second ends and a predetermined length between the first and second ends, entrapped in a winding interface between turns of the coiled wire and the outer wall of the hollow tube extension in an entrapment zone intermediate the first and second ends.

The inventive rotating brush described in the '653 patent has flexible brush bristles extending outward from a brush shaft or distal drive shaft end in all directions. The brush is attached to the elongated, flexible, rotatable drive shaft or brush shaft which is attached at its proximal end to a drive motor to impart rotary motion to the brush shaft and bristles. The system includes a brush delivery catheter adapted to be introduced and advanced through a patient's blood vessels until the distal end is positioned adjacent the soft fibrinous thrombus. Once the brush delivery catheter is positioned, the brush bristles and brush shaft are passed through the brush delivery catheter lumen and out its distal opening to place the brush in contact with the soft thrombus. The bristles are sufficiently resilient and dimensioned for allowing compression and passage out of and back into the distal opening of the brush delivery lumen and for mixing into and macerating the fibrin of the soft thrombus, without damaging a vessel wall.

In one embodiment described in the '653 patent, the brush shaft is hollow to define a brush shaft lumen and preferably is formed with a penetrable distal tip valve normally closing the distal end opening of the brush shaft lumen. The thrombolytic agent is optionally delivered through the brush shaft lumen and through side exit holes or ports into the region of the brush bristles. The brush shaft lumen allows the advancement of the brush over a previously introduced and positioned guidewire to a thrombus in a blood vessel or the lumen of a medical implant. The brush shaft lumen also allows for the advancement of a miniaturized blood flow obstruction microcatheter through it and distally of the obstruction. It is proposed that proximal and distal penetrable valves be provided at the proximal and distal drive shaft lumen end openings to seal against the backflow of blood and thrombolytic agent while the microcatheter or guidewire is present or is absent from the drive shaft lumen. In practice, the guidewire and microcatheter O.D. and the drive shaft lumen I.D. are closely dimensioned, and it is difficult to fabricate such seals that function effectively.

In another embodiment disclosed in the '653 patent, the brush drive shaft is solid, and the dissolving agent is introduced through the brush delivery catheter lumen alongside the drive shaft lumen while the brush drive shaft is rotated. The thrombolytic agent is emitted from the distal end opening of the brush delivery catheter lumen in the region of rotation of the brush bristles for dissolving the soft thrombus exposed by the rotating brush bristles.

The assignee of the '653 and '355 patents and the present application has implemented the solid drive shaft brush embodiment of the '653 patent in the Cragg Thrombolytic Brush™. The Cragg Thrombolytic Brush™ is presently used in the lumen of an A/V graft implanted in a patient's vascular system for hemodialysis to dissolve thrombi that form therein. The Cragg Thrombolytic Brush™ is described and depicted in "The Thrombolytic Brush", by Andrew H Cragg, MD presented at *The Second Mid-Atlantic Conference on Angio Access: Establishment and Maintenance of Dialysis and Venous Access*, Williamsburg, Va. (pp. 162–165 of proceedings) in October 1996 and in product literature published by the assignee in 1997.

In the Cragg Thrombolytic Brush™ embodiment, the brush and brush drive shaft are enclosed within the brush delivery catheter as a sub-assembly that allows the brush to be garaged in the brush delivery catheter lumen as it is advanced to the graft lumen and to be advanced out of the catheter lumen distal end opening. The brush sub-assembly includes a Y-connector at the proximal end of the brush delivery catheter that has a Y-connector lumen that the brush drive shaft passes through. The Y-connector includes a side port coupled to an infusion port for allowing thrombolytic agent to be introduced into the Y-connector lumen and then distally down the annular space between the brush drive shaft and the brush delivery catheter lumen. The proximal end of the Y-connector includes a seal for sealing around the brush drive shaft to prevent leakage of the infused thrombolytic agent and a threaded luer connector having a proximal luer hub that fits into an annular recess in the housing of the drive motor unit.

An enlarged male shaft hub is formed at the proximal end of the brush drive shaft that is inserted axially through a central opening of the annular recess and into engagement with a female bore aligned with the central opening. The female bore is integrally formed within a driven gear that is rotated by a drive gear coupled with the drive motor. As the shaft hub is seated into the female bore, the brush sub-assembly and the drive motor unit are brought together to fit the luer hub proximal end into the annular recess of the drive motor unit. The drive motor unit and the hub are rotated with respect to one another to rigidly attach them together. The brush is ejected distally from the brush delivery catheter lumen.

At this point, the brush delivery catheter and brush drive shaft are extended through the patient's vascular system and it is undesirable to rotate them within the vascular system. It is therefore necessary to rotate the drive motor unit while holding the brush sub-assembly still in order the attach the luer lock elements together. It is not always possible to know in advance just how the drive motor unit will be aligned with respect to the side port of the Y-connector when the attachment is finished. Thus, the attachment process and any adjustment has to be done carefully and relatively slowly to arrive at a suitable final attachment orientation.

There are many advantages to employing a hollow lumen brush body that can be introduced over a previously placed guidewire and that can be used with other miniature catheters and infusion wires as described in the above-incorporated '653 patent. The brush body lumen distal end opening can either be open or have a distal seal that is penetrable by such devices as described above. However, in use, blood and thrombolytic agent backflows proximally through the brush drive shaft lumen and can infiltrate the drive motor unit and cause it to fail.

A need exists for a simple manner of sealing the drive motor unit from infiltration of blood and thrombolytic agent that backflows through the drive shaft lumen while keeping the lumen open to receive guidewires and other devices.

In addition, it is conceived that it is often desirable to connect and disconnect the brush sub-assembly from the drive motor unit during a medical procedure. At times it is desirable to remove or insert a guidewire or other device from or into the proximal end opening of the drive shaft lumen while it is either attached to or separated from the drive motor unit.

SUMMARY OF THE INVENTION

It is therefore an object of the present invention to provide such a sealing mechanism for a hollow lumen drive shaft for sealing the drive motor unit from infiltration of fluids, e.g. blood and infusate, that backflow through the drive shaft lumen while keeping the lumen open to receive guidewires and other devices.

It is a further object of the present invention to provide such a sealing mechanism that is effective upon seating of an obstruction treatment device or brush sub-assembly with a drive motor unit so that the sub-assembly can be rotated by the drive motor unit.

It is another object of the present invention to provide such a sealing mechanism in conjunction with an attachment mechanism that is adapted to precisely axially align a hollow brush drive shaft with drive and sealing components of the drive motor unit.

It is still another object of the present invention to provide a guide mechanism within the drive motor unit for guiding the insertion of guidewires or microcatheters or other elongated medical devices proximally and/or distally through the drive motor lumen of the drive motor unit.

In accordance with these and other objects, a motor and obstruction treatment device sub-assembly, particularly a brush assembly preferably for use in thrombectomy procedures, is provided with a precise, positive and repeatable attachment mechanism of the sub-assembly with the drive motor unit that is simple to attach and detach and guides the attachment and/or effects a seal about the drive shaft that prevents infiltration of body fluids and infusate into the drive motor unit.

The elongated, flexible, rotatable drive shaft extends from a proximal drive shaft end to a distal drive shaft end and is formed with a drive shaft lumen extending through its length between lumen openings at the proximal and distal drive shaft ends. An elongated, flexible, distal drive shaft section in which the brush (or other obstruction treatment device) is formed is dimensioned to fit within a catheter lumen of a brush and thrombolytic agent delivery catheter. A proximal drive member is formed in a portion of the drive shaft proximal to the distal drive shaft section and is configured to be received in a drive motor lumen of the drive motor unit. When the proximal drive member is received in and seated in the drive motor lumen, it engages drive components of the drive motor unit for rotating the drive shaft and brush and the proximal drive shaft end is accessible from a proximal drive motor lumen end opening.

The brush (or other obstruction treatment device) can be retracted proximally into the brush drive shaft lumen when the proximal drive member is not received and seated in the drive motor lumen. The brush can thereby be garaged therein to facilitate introduction of the brush of the brush sub-assembly to a site of a soft obstruction. The brush drive shaft can also be manually advanced distally in the same path to distally extend the brush out of the catheter lumen distal end opening. In accordance with a further aspect of the invention, the brush and a distal portion of the brush drive shaft distal section are automatically extended out of the catheter lumen distal end opening when the drive member is received in and seated in the drive motor lumen.

The hand held drive motor unit is formed with a distal drive motor lumen end opening for receiving the proximal drive member of the brush sub-assembly and with a proximal drive motor lumen end opening for providing access to the drive shaft proximal end. When the proximal drive member is received in the drive motor lumen, the rotatable proximal drive shaft end extends through a seal along the drive motor lumen distal to the proximal drive motor lumen end opening. The seal is dynamically operable during rotation of the drive shaft to prevent infiltration of body fluids and infusate transmitted through the drive shaft lumen from the distal drive shaft lumen end opening to the proximal drive shaft lumen end opening and then into the drive motor unit.

The drive shaft lumen receives an elongated medical device, e.g., a microcatheter or guidewire, for over-the-wire introduction of the brush drive shaft and the surrounding brush delivery catheter to a site in a patient's body, e.g., through a vascular access device lumen and into a blood vessel or vascular implant lumen. The drive motor lumen is also configured with guides to facilitate passage of a guidewire distally and proximally through it when the proximal drive member is removed from the drive motor lumen. The microcatheter or guidewire can be inserted into the distal drive motor lumen end opening and advanced proximally and out of the proximal drive motor lumen end opening while guided by distal guides within the drive motor lumen. The microcatheter or guidewire can similarly be inserted into the proximal drive motor lumen end opening and advanced distally and out of the distal drive motor lumen end opening while guided by proximal guides within the drive motor lumen.

In one use of the preferred embodiment, a guidewire is advanced to the site of a soft obstruction in a blood vessel lumen or the lumen of a medical implant. The proximal end of the guidewire is inserted into the drive shaft lumen distal end opening, and the drive shaft and delivery catheter are advanced over the guidewire to the site. While the over-the-wire advancement can be performed with the brush sub-assembly coupled with the drive motor unit, doing so requires that the brush be extended from the delivery catheter lumen distal end opening. It is preferred that the brush be garaged within a distal end section of the brush delivery catheter lumen during the advancement to the site.

After the brush is advanced to the site, the proximal end of the guidewire is inserted into the drive motor unit lumen distal end opening. The drive motor unit is advanced distally over the guidewire until the proximal end of the guidewire passes through the seal and extends proximally from the drive motor unit lumen proximal end opening.

Then, the proximal drive member is axially aligned with and inserted axially into the distal drive motor lumen end opening and seated therein while being guided by the distal guides and engaging the drive components and the dynamic seal. The dynamic seal seals the proximal drive motor lumen end opening from the back flow of blood and infusate or thrombolytic agent through the drive shaft lumen. The sub-assembly connector and the drive motor unit connector positively lock together upon axial insertion and mutual engagement of the connectors. The mutual engagement of the connectors preferably allows full 360° rotation of the brush sub-assembly with respect to the drive motor unit to a selected angular alignment. The mutual engagement of the connectors allows the proximal drive member to be rotated by the drive motor unit at any selected angular alignment of the brush sub-assembly with respect to the drive motor unit.

In this manner, the brush is advanced out of the brush delivery catheter lumen and positioned in relation to an elongated soft obstruction. The drive shaft is rotated by energizing the drive motor in a prescribed rotation direction, and the brush is retracted proximally through the soft obstruction. A thrombolytic agent is delivered from a side port of a Y-connector and through the brush delivery catheter lumen alongside the drive shaft and out of the delivery catheter distal end opening adjacent to the brush. The fibrin of the soft obstruction is macerated by the rotating brush bristles into particles or otherwise exposed as the thrombolytic agent is delivered.

The guidewire can also be withdrawn proximally and reinserted and advanced distally through the drive shaft lumen if necessary. Or a further elongated medical device can be inserted through the accessible proximal drive shaft lumen end opening. The guidewire can also be inserted into and extended distally through the drive motor unit lumen from the distal drive motor lumen end opening when the brush sub-assembly is not attached.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other objects, advantages and features of the invention will become apparent from the following detailed description of the preferred embodiments of the invention, in which.

DETAILED DESCRIPTION OF THE PREFERRED EMBODIMENT OF THE INVENTION

In view of the apparent interchangeable use in the background art, only the terms "soft obstruction" or "thrombus"

and "thrombectomy" will be employed in the following description of the preferred embodiment of the invention, and it will be understood that these terms shall embrace and be the equivalent of blood clot or embolus and embolectomy, respectively, and are applicable to the removal of soft, recently formed emboli, thrombi or blood clots.

Figure 1:
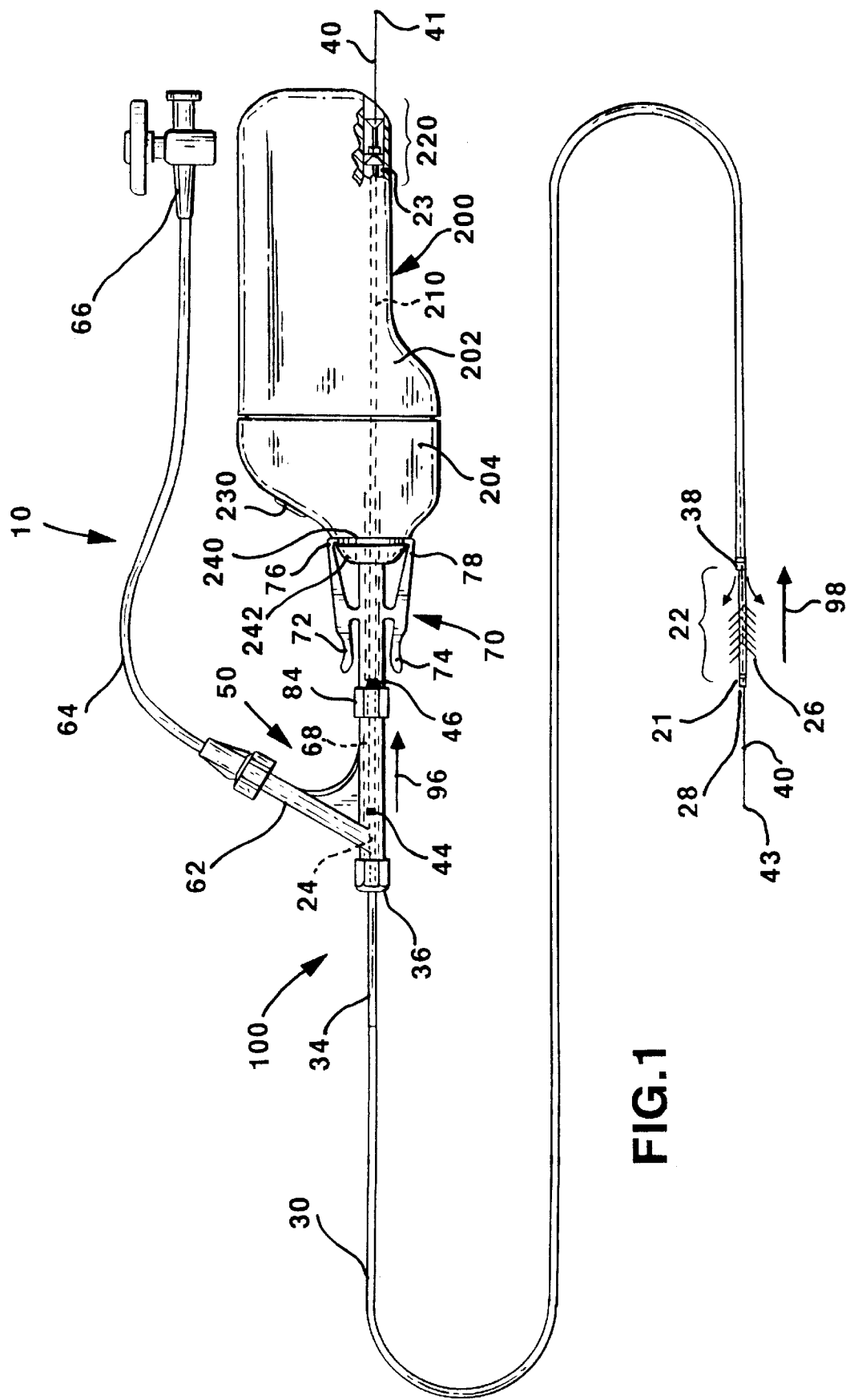
FIG. 1 is a plan view of a preferred embodiment of the motor and brush assembly of the present invention.

FIG. 1 illustrates a motor and brush assembly 10 which incorporates one embodiment of a dynamic seal assembly 220 for sealing the interior of a drive motor unit 200 from the backflow of blood and thrombolytic agent through a hollow lumen brush drive shaft 20 when the brush sub-assembly 100 is attached with the drive motor unit 200. The dynamic seal assembly 220 allows rotation of the brush drive shaft with respect to the drive motor unit 200. Moreover, it is located in and forms part of a drive motor lumen 210 that is formed with proximal and distal guides described below. The proximal and distal guides allow the guidewire 40 or a microcatheter dimensioned to fit within the drive shaft lumen of the brush drive shaft 20 to be inserted distally or proximally, respectively, through the drive motor lumen 210 when the brush sub-assembly is not attached to the drive motor unit 200.

Figure 2:
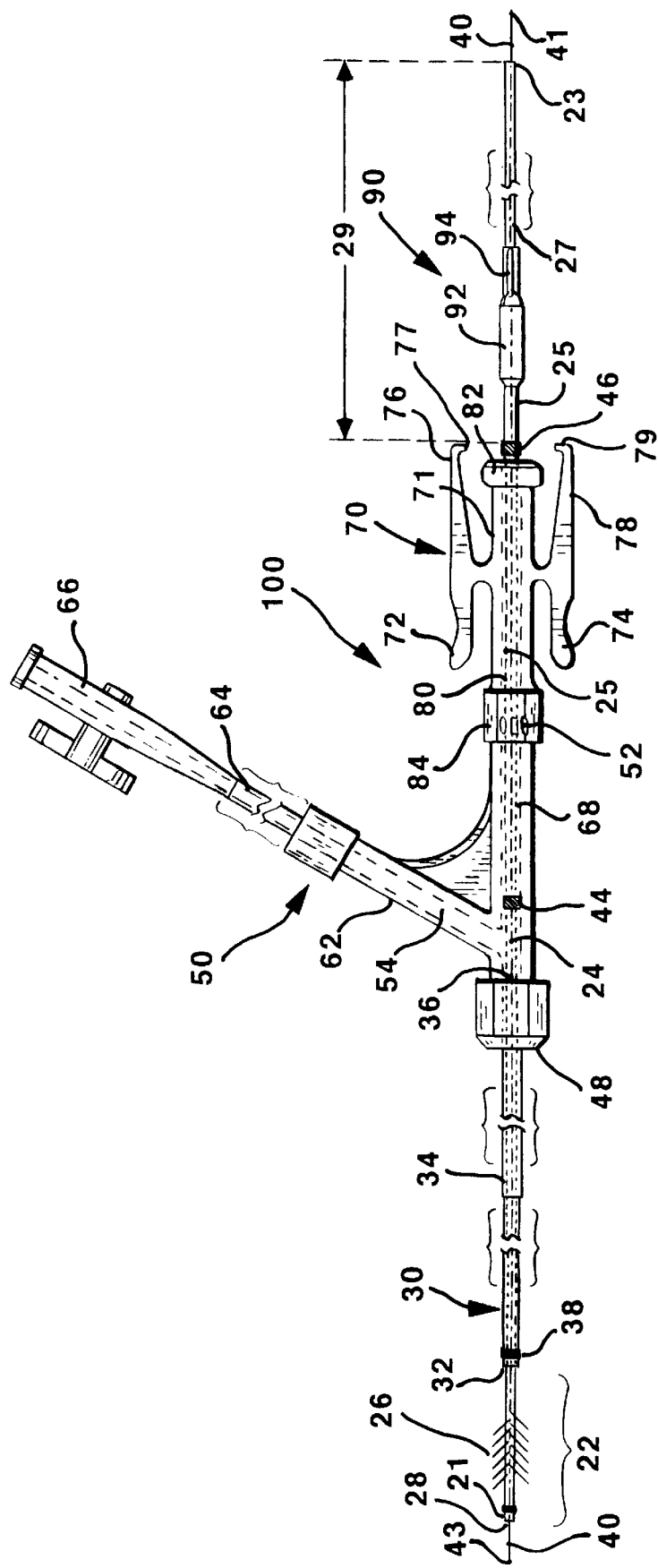
FIG. 2 is an enlarged, plan view of the brush sub-assembly depicting the clip connector of the embodiment of the invention.
Figure 3:
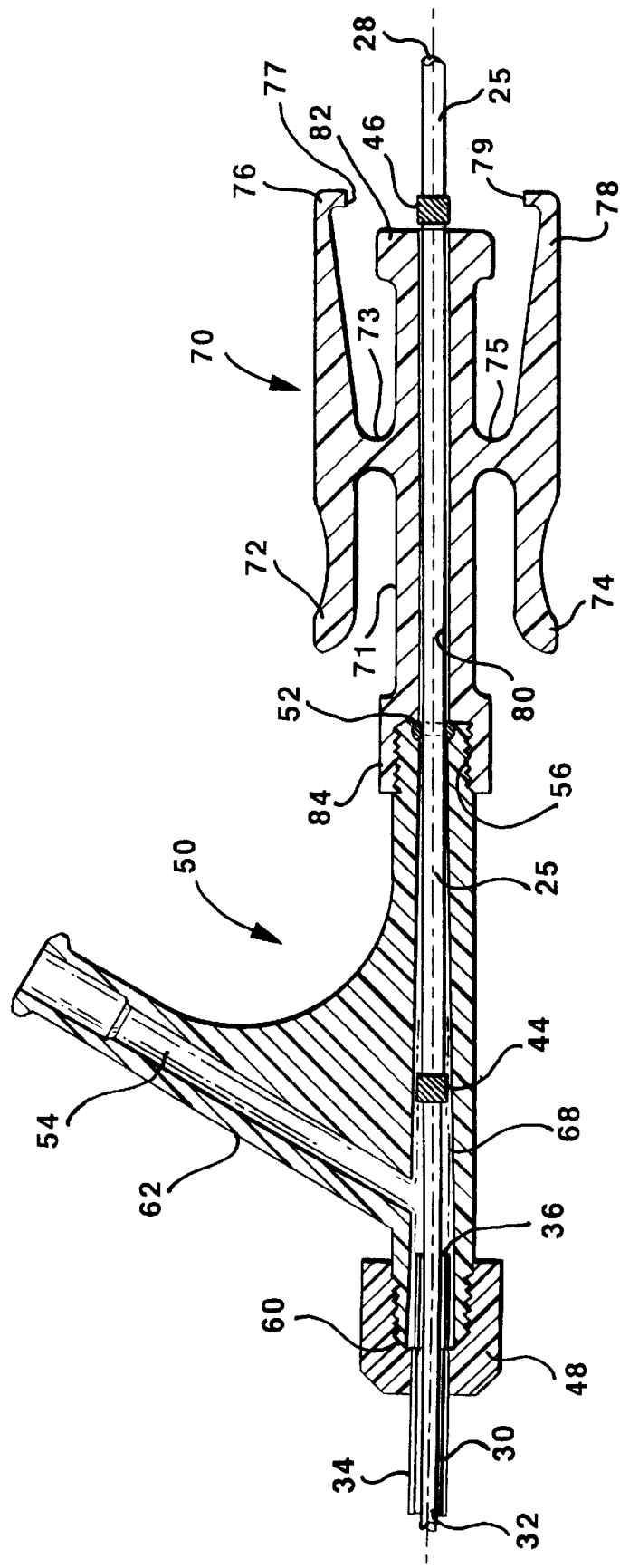
FIG. 3 is a cross-section view of the clip connector of the embodiment of the invention and an attached Y-connector taken along lines 3—3 of FIG. 2.

The brush sub-assembly 100, including the brush drive shaft 20, the brush delivery catheter 30, a clip connector 70 and a Y-connector 50 is also depicted separately in FIG. 2 and in FIG. 3 in part. The brush drive shaft 20 extends from its proximal end 23 to its distal end 21 through the clip connector lumen 80 of clip connector 70, the Y-connector lumen 68 of Y-connector 50 and the delivery catheter lumen 32 of delivery catheter 30. The drive shaft 20 is formed of a number of sections that are attached together in tandem and provide a continuous drive shaft lumen 28. The continuous drive shaft lumen 28 extends all the way from the drive shaft lumen proximal end opening at the proximal drive shaft end 23 to the drive shaft lumen distal end opening at distal drive shaft end 21 in which the microcatheter or guidewire 40 can be received. The drive shaft sections include a relatively long flexible, distal drive shaft section 24, a relatively short and stiff, intermediate drive shaft section 25, and a further relatively short and stiff, proximal drive shaft section 27.

The distal drive shaft section 24 is preferably formed of thin wall tube having a 1.4 mm O.D. and a 1.0 mm drive shaft lumen I.D., the thin wall tube formed of a polyether amide coated over stainless steel wire braid. A distal drive shaft portion 22 of the distal drive shaft section 24 extends outward of the distal end opening of the brush delivery catheter 30 when the brush sub-assembly 100 is attached to the drive motor unit 200 as shown in FIG. 1. The brush 26 is formed around the periphery of the distal drive shaft portion 22 that can be retracted into the brush delivery catheter lumen 32 when the brush sub-assembly 100 is not attached to the drive motor unit 200 in a manner described below. The brush bristles may take the form of those described in the above-incorporated '653 or '355 patents or the embodiments disclosed in the above-referenced '(9135390.APP) application.

The intermediate drive shaft section 25 is preferably formed of a hypotube, e.g., a stainless steel tube, that is coated with polytetrafluoroethylene (PTFE) and has a tube lumen with a tube lumen I.D. dimensioned to receive the proximal end of the relatively flexible distal drive shaft section 24. An enlarged, annular, distal stop 44 is formed at the junction of the proximal end of the distal drive shaft section 24 and the distal end of the intermediate drive shaft section 25 as shown in FIGS. 2 and 3. The intermediate drive shaft section extends proximally through the Y-connector lumen 68 and then through the clip connector lumen 72 and extends proximally therefrom a further predetermined distance to its proximal end within a drive hub 90. An enlarged, annular, proximal stop 46 is formed at a predetermined point along the length of the intermediate drive shaft section 25.

The proximal drive shaft section 27 is also preferably formed of a hypotube, e.g., a stainless steel tube, that is also coated with PTFE that has a tube O.D. and tube lumen I.D. similar to those of the distal drive shaft section 24. The distal end of the proximal drive shaft section 27 is inserted into the tube lumen of the intermediate drive shaft section, and the drive hub 90 is formed over the junction of the proximal and intermediate drive shaft sections. The proximal drive shaft section 27 extends from that junction a predetermined distance to the proximal drive shaft end 23.

In FIG. 2, the proximal drive shaft section 27 and a distal portion of the intermediate drive shaft section extending to the proximal stop 46 constitute a proximal drive portion 29 of the drive shaft 20. In FIG. 1, the proximal drive portion 29 extends through the schematically illustrated drive motor lumen 210 of the drive motor unit 200 with the proximal drive shaft end 23 seated within seal assembly 220. The dimensions between the proximal drive shaft end 23 and the drive hub 90 and the proximal stop 46 are selected to match the overall length of the drive motor lumen 210 drive components engaging the drive hub 90 as described below. The drive hub 90, shown in FIG. 2, is dimensioned and formed about the proximal drive shaft section 24 and spaced distally from proximal drive shaft end 23 sufficiently to be engaged in a drive chuck along the drive motor lumen 210 when the proximal drive shaft end 23 is seated as shown in FIG. 1. The drive hub 90 is formed of an elongated distal cylinder 92 surrounding the drive shaft surface and an elongated proximal, square cross section bar 94 molded as a single piece over the junction of the distal and proximal ends of the proximal and intermediate drive shaft sections 27 and 25, respectively.

The drive shaft 20 is trapped within the aligned brush delivery catheter lumen 32, Y-connector lumen 68 and clip connector lumen 80 so that it cannot be removed therefrom. The distal and proximal stops 44 and 46, respectively, are located a precise distance apart from one another and from the drive hub 90 and proximal drive shaft end 23 along the intermediate drive shaft section 25. The distal stop 44 fits within the Y-connector lumen 68, and the proximal stop 46 is located proximal to the proximal annular seat 82 and is greater in diameter than the clip connector lumen 80. The stops 44 and 46 allow the drive shaft 20 to be advanced distally within the aligned lumens 32, 68 and 80 until the distal stop 46 engages against the proximal surface of the proximal annular seat 82 and advanced proximally until the distal stop 44 engages against a narrowed proximal end of the Y-connector lumen. A limited longitudinal travel sufficient to allow the brush 26 to be retracted proximally in the direction of arrows 96 and 98 of FIG. 1 and garaged within a distal section of the of the brush delivery catheter lumen 32 is thereby provided.

The brush sub-assembly 100 further includes the brush delivery catheter 30 having a catheter lumen 32 for receiving the distal drive shaft section 24 including the distal drive shaft portion upon which the brush 26 is formed. The brush delivery catheter 30 is reinforced by a reinforcing tube 34 for providing stress relief extending distally a short distance from its proximal end 36. The reinforced proximal end 36 of the brush delivery catheter 30 is attached to the threaded distal end 60 of a Y-connector 50 through use of a threaded compression cap 48 as shown in FIG. 3. In this way, the brush delivery catheter lumen 32 is aligned with the Y-connector lumen 68. The brush delivery catheter 30 preferably may be about 65 cm to about 115 cm long, and have a 6 French (2.06 mm) O.D. and a lumen I.D. of about 1.73 mm. The brush delivery catheter 30 preferably is formed of a tubular wire braid that is encased in a plastic material and is relatively flexible. The brush delivery catheter distal end 38 preferably has a radiopaque ring or band formed around the distal end opening of the brush delivery catheter lumen 32.

A side port extension 62 of Y-connector 50 provides a fluid coupling with the brush delivery catheter lumen 32 via the Y-connector lumen 68 and the side port lumen 54. A flexible extension tube 64 extends from the side port extension 62 and terminates in an infusion port 66 for attachment to a source of thrombolytic agent (not shown).

The clip connector 70 constitutes one preferred embodiment of a brush sub-assembly connector and is coupled by a threaded distal coupling 84 to the threaded proximal end 56 of the Y-connector 50. A clip connector barrel 71 surrounds a constant diameter clip connector lumen 80 that is thereby aligned with the Y-connector lumen 68. An O-ring 52 is trapped in an annular recess within the lumen 68 at the threaded proximal end 56. The O-ring lumen tightly receives and bears against the intermediate brush drive shaft section 25 extending through the lumens 68 and 80. The clip connector lumen 80 extends to the proximal end opening thereof within an enlarged proximal annular seat 82. The threaded female couplings 48 and 84 are tightly screwed onto the threaded male ends 60 and 56, respectively, and adhesive may be applied to assure that the attached components cannot loosen and rotate.

The clip connector 70 further comprises a pair of moment arms 76 and 78 joined by hinges 73 and 75, respectively, disposed at 180° apart positions on the circumference of the clip connector barrel 71 and extending proximally to either side of the proximal annular seat 82. The free clip ends 77 and 79 of the moment arms 76 and 78, respectively are turned inward extending radially toward one another and the axis of the connector barrel 71 to form attachment clips. The free clip ends 77 and 79 are biased by the hinges 73 and 75 to have a pre-determined separation apart from one another. The moment arms 76 and 78 also extend distally from hinges 73 and 75, respectively, to finger grips 72 and 74, respectively. The hinges 73 and 75 are resilient enough to allow finger grips 72 and 74 to be squeezed together toward the barrel 71 to increase the separation of the free clip ends 77 and 79, respectively. The interaction of the free clip ends 76 and 78 with a circular retention groove 240 of drive motor unit 200 allows the attachment of the brush sub-assembly 100 with the drive motor unit 200 as described below.

A guidewire 40 is shown in FIGS. 1 and 2 extending from the distal and proximal end openings of the distal and proximal ends 21 and 23 of the drive shaft lumen 28. In FIG. 1, the guidewire 40 is depicted exiting the proximal end opening of the drive motor lumen 210. It will be understood that the guidewire 40 is provided for over-the-wire introduction and positioning of the distal end of the brush sub-assembly 100 in relation to a soft obstruction in a blood vessel or a vascular access device or the like. The guidewire 40 may be withdrawn during rotation of the brush 26, or may be left in place as described below.

Returning to the drive motor unit 200 shown in FIG. 1, it includes a battery powered drive motor, gear assembly, and a drive chuck aligned with the drive motor lumen 210 of the drive motor unit 200. The drive motor lumen 210 is schematically depicted extending in alignment with the Y-connector lumen 68 and the clip connector lumen 80. The drive motor lumen 210 terminates proximally with the proximal seal assembly 220 (shown in partial cross-section) that seals the interior of drive motor unit 200 from blood escaping from the proximal end opening of the drive shaft lumen 28.

It will be understood that drive motor unit 200 only rotates the hollow lumen drive shaft 20 and the brush 26 formed about distal drive shaft section 22. The internal drive motor is turned on by depression of push-button switch 230 which closes and provides battery power to the internal drive motor. In a thrombectomy application, the internal drive motor rotates the drive shaft 20 relatively slowly, on the order of about 500–3000 RPM and in a single direction.

As noted above, a thrombolytic agent is delivered into the space in Y-connector lumen 68 outside of the outer surface of the proximal drive shaft section 24 shown in FIG. 3. The trapped O-ring 52 within compression cap 84 provides a rotary seal within the proximal end of the Y-connector 50 for sealing around the exterior surface of the proximal drive shaft section 24. The compressed O-ring 52 inhibits the back flow of thrombolytic agent or blood through the clip connector lumen 80 and into the drive motor lumen 210. The thrombolytic agent is forced distally through the annular space between the outer surface of the proximal drive shaft section 24 and the inner surface of the brush delivery catheter 30 until it escapes from the annular opening at the brush delivery catheter distal end 38.

The rotation of the brush 26 to separate and mix the fibrin of a soft obstruction while a thrombolytic agent is supplied to it generally follows the teachings of the above-incorporated '653 patent. The attachment mechanisms, the proximal seal assembly 220, and other features of the drive motor unit 200 of the present invention are not disclosed in the above-incorporated '653 and '355 patents or employed in the earlier above-referenced Cragg Thrombolytic Brush™ system.

FIGS. 4–8 depict the components and construction of the drive motor unit 200 in greater detail. The drive motor unit 200 is formed with a proximal housing section 202 and a distal housing section 204 that are molded of plastic material and adhered together at an overlapping seam 206. The proximal housing section 202 is formed with a receptacle 208 and pin 212 for receiving an integral battery and DC drive motor 214. The battery and drive motor 214 are coupled electrically to a switch button 230 in housing half section 204 which applies battery power to the drive motor to rotate the drive shaft 262 and the drive gear 264 attached to it.

The teeth of the drive gear 264 mesh with teeth of a driven gear 274 which is formed integrally with a chuck body 270 for receiving the drive shaft hub 90. The integral chuck and driven gear unit 290 is supported to be in axial alignment with and define part of the drive motor lumen 210. The drive motor lumen 210 extends between the proximal lumen end opening 248 and the distal lumen end opening 246. First and second proximal lumen cylindrical bores 250 and 252 extend distally from the proximal drive motor lumen end opening 248 to a conical guide 252 that surrounds a bore 256 through the end of the first cylindrical bore 250. The second cylindrical bore 252 houses the components of the dynamic seal 220.

Figure 6:
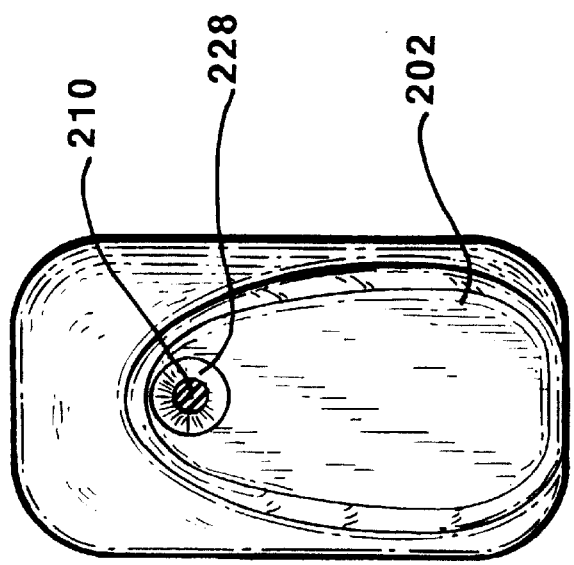
FIG. 6 is a proximal end view of the drive motor unit of FIG. 1.
Figures 7, 8:
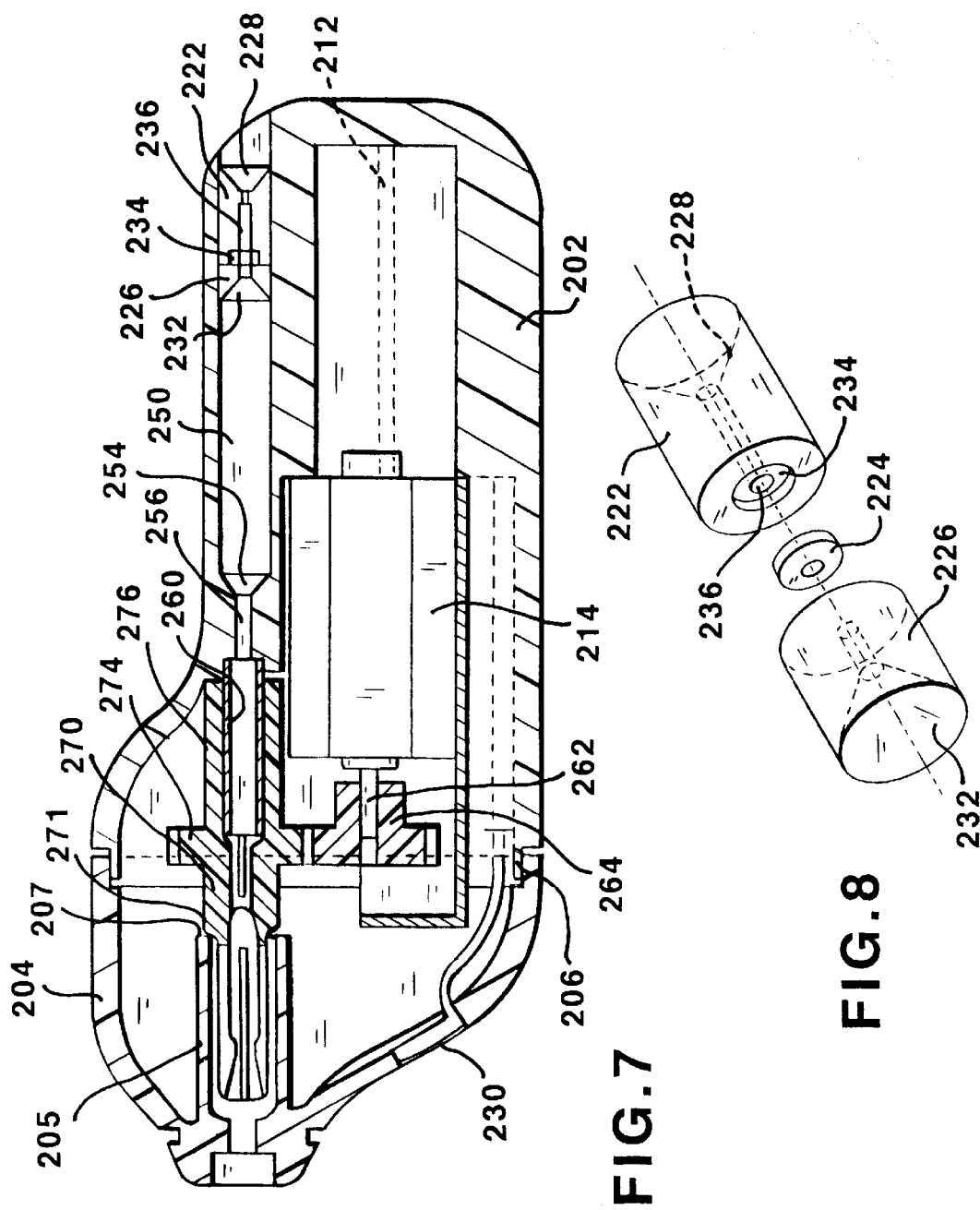
FIG. 7 is a side partial cross-section view of the drive motor unit of FIG. 1 depicting the arrangement for receiving the brush proximal drive shaft end and for attachment with the clip connector of the brush sub-assembly.
FIG. 8 is an exploded, enlarged, perspective view of the components of the dynamic rear seal that fits in the drive motor lumen and seals the interior components of the drive motor unit from blood that backflows through the drive shaft lumen during use of the motor and brush assembly.

The dynamic seal 220 is also shown in the end view of FIG. 6 and the perspective view of FIG. 8. The dynamic seal and is formed of a rigid plastic proximal cylindrical guide member 222, a rigid plastic distal cylindrical guide member 226 and a soft silicone rubber annular O-ring 224. The proximal guide member 222 has an axial bore 236 extending through it from a conical or funnel shaped, proximal guide 228 formed in its proximal surface to an annular seat 234 formed in its distal surface. The distal guide member 226 has a funnel or conical shaped, distal guide 232 formed in its distal surface. The O-ring 224 is trapped between members 222 and 226 in the seat 224 and it forms a seal orifice that bears against the outer surface of drive shaft proximal section 24 when it is inserted through it and its proximal end 23 seated proximally to the location of the O-ring 224. The dynamic seal 220 is axially inserted into the second bore 252 until it abuts the distal end thereof and is sealed in place.

Figure 4:
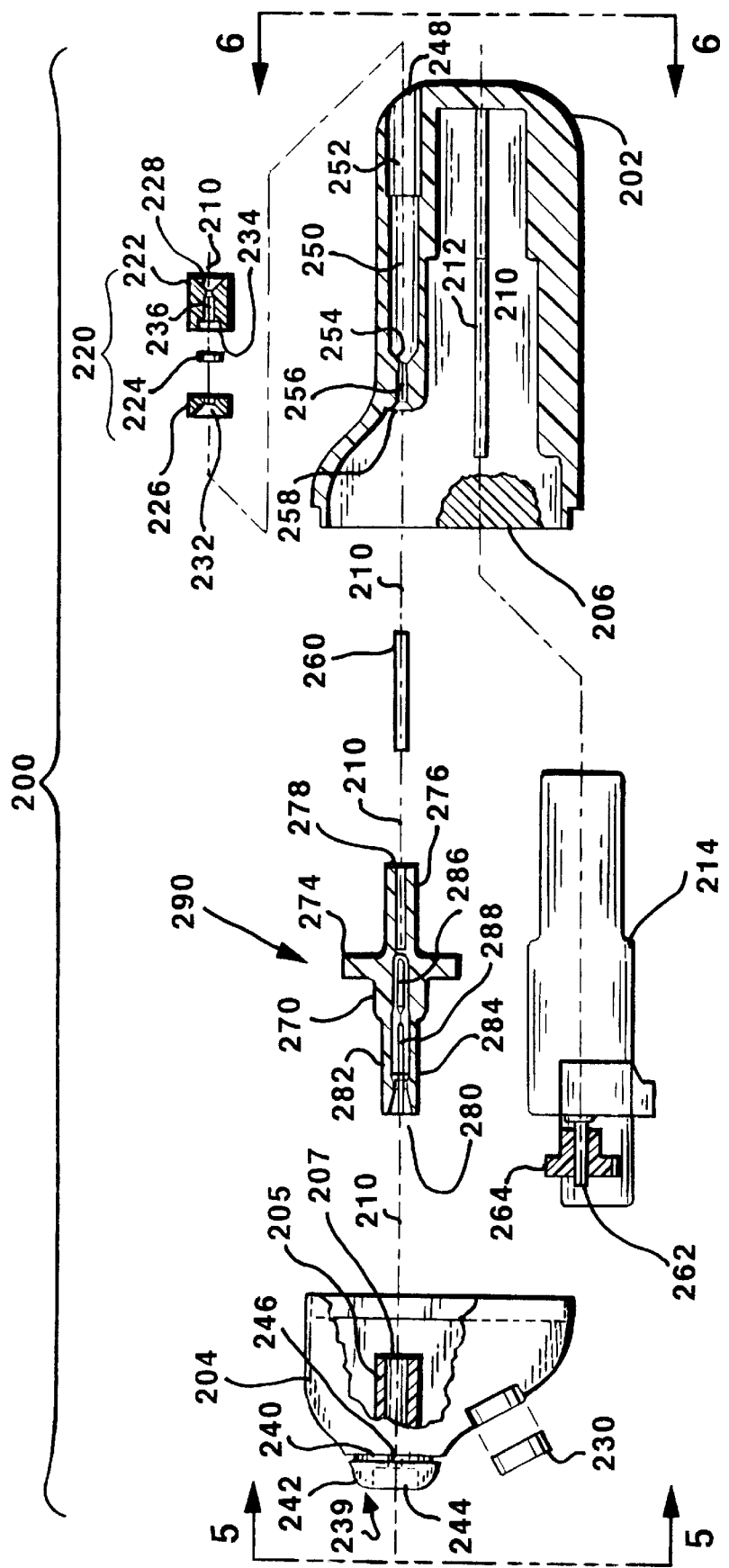
FIG. 4 is an exploded view of components of the drive motor unit of FIG. 1.

The integral chuck and driven gear unit 290 is supported to be in alignment with and define part of the drive motor lumen 210 by cooperation with a distal support tube 205 (shown in FIG. 7) and a proximal support tube 260. The distal support tube 205 is formed integrally with the distal housing section 204 and extends proximally therein and in axial alignment with the drive motor lumen 210 and distal drive motor lumen end opening 246. The free end 207 of the distal support tube 205 provides a bearing surface for engagement against an annular distal shoulder 271 of the integral chuck and driven gear unit 290. A distal end of the proximal support tube 260 is pressed into the bore 278 of the proximal axis extension 276 of the integral chuck and driven gear unit 290. The proximal end of the support tube 260 bears against an annular seat 258 surrounding the bore 256. The lumen diameter of the support tube 260 is sized to allow passage of the brush drive shaft proximal section 24 therethrough. When the components of FIG. 4 are fitted together in the manner shown in FIG. 7, the drive motor lumen 210 is formed, and the teeth of the drive gear 264 mesh with the teeth of the driven gear 274.

Figure 11:
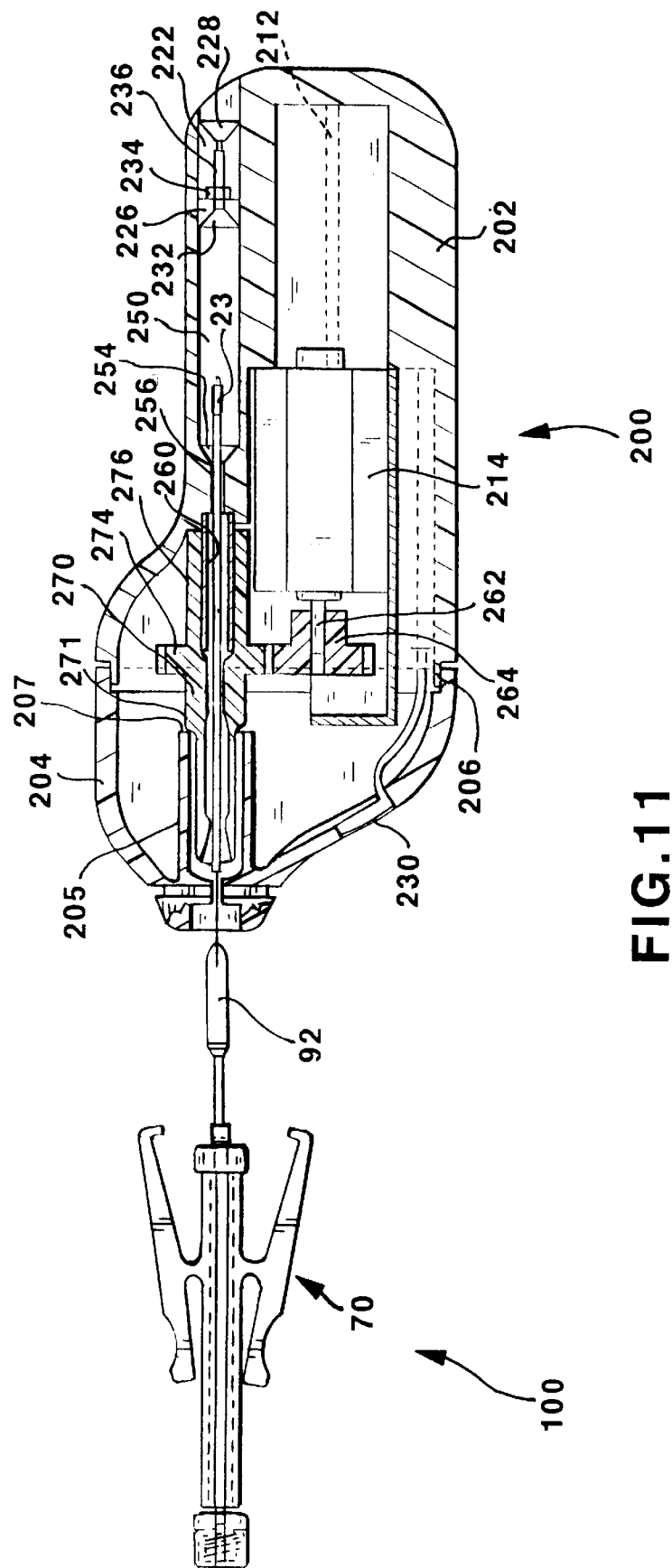
FIG. 11 depicts the partial advancement of the brush shaft proximal end into the drive motor lumen over the guidewire and the separation of the clip free ends of the clip connector as they ride upon the cam surface of the drive motor housing.

The integral chuck and driven gear unit 290 also comprises the expandable drive chuck 280 which is formed of four 90° section chuck elements that together encircle a circular bore 288. Two of the chuck elements 282 and 284 are depicted in the cross-section view. The four chuck elements are attached at their proximal ends to the chuck body 270 and extend distally to free ends that are tapered to form a conical distal entrance into the circular chuck bore 288. The proximal end of the circular bore 288 is aligned with the square chuck bore 286. The circular and square chuck bores are dimensioned to receive the cylinder 92 and bar 94, respectively, of the drive hub 90. The four chuck elements spread apart at their free ends within the bore of tube 205 as the hemispheric ends of the cylinder 92 are pushed against them proximally during insertion and or pulled against them distally during retraction as shown in FIG. 11.

Figure 5:
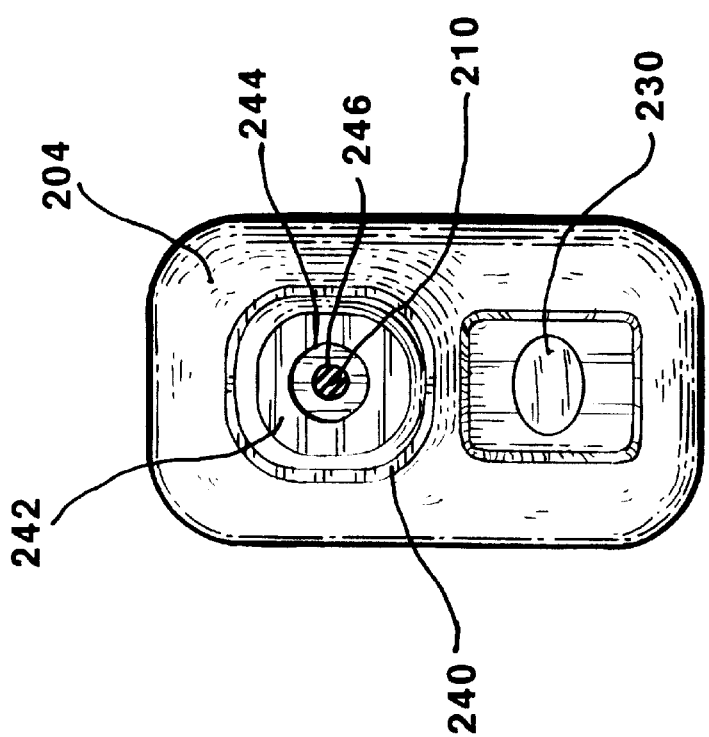
FIG. 5 is a distal end view of the drive motor unit of FIG. 1.

In the first preferred embodiment of the drive motor unit connector 239, the drive motor unit housing 204 is formed with an annular, dome shaped projection surrounding the drive motor unit distal end opening 246 as shown also in FIG. 5. The dome shaped projection provides a cam surface 242 of increasing diameter radially from the axis of the drive motor unit lumen 210. The cam surface 242 is maximally bounded by an annular retention groove 240 recessed into the drive motor unit housing. An annular, proximally extending receptacle 244 is formed within the dome shaped projection that also surrounds the drive motor unit distal end opening 246. The annular retention groove 240 surrounding the annular receptacle 244, the annular receptacle 244, and the cam surface 242 extending therebetween comprise the drive motor unit connector 239.

Figure 9:
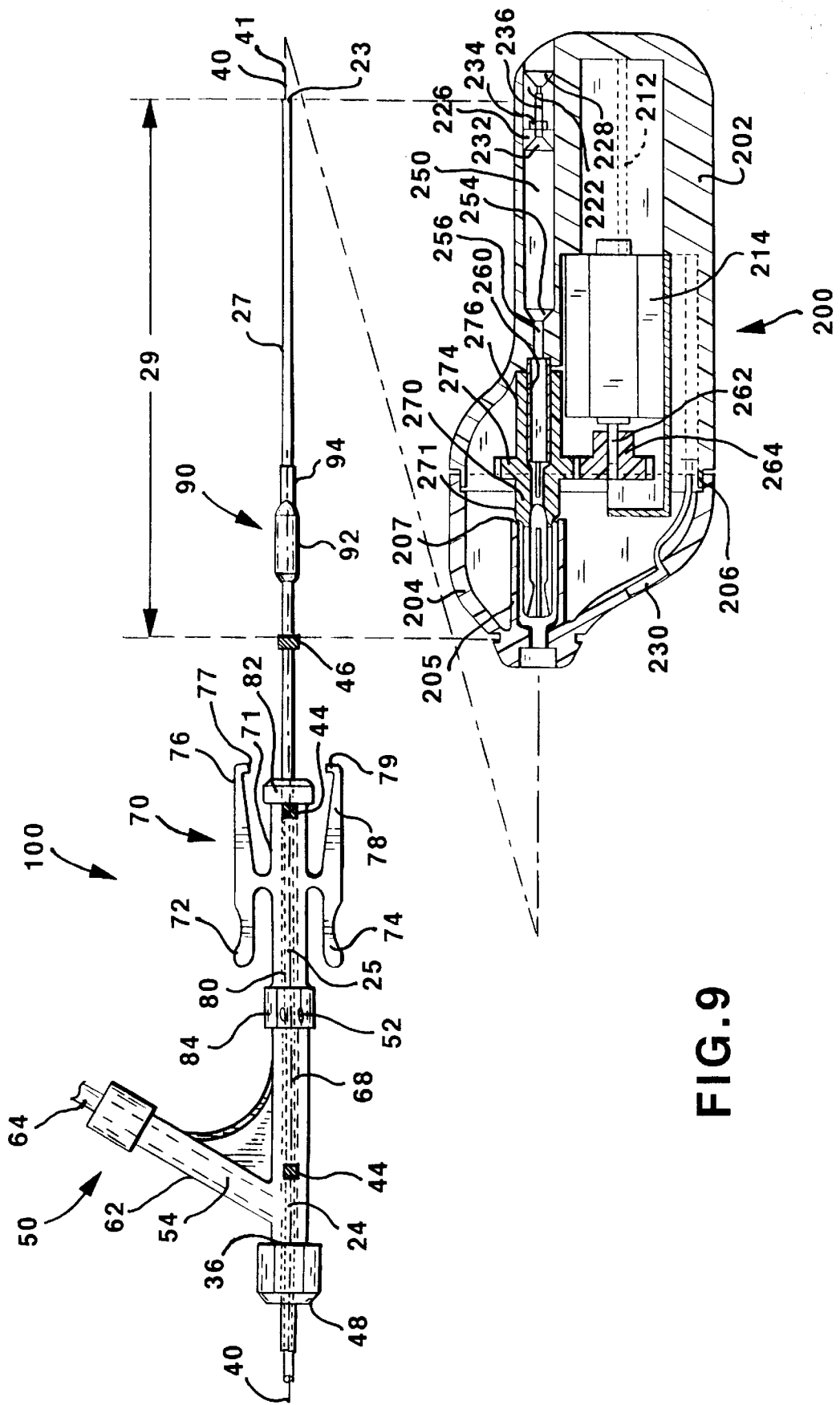
FIG. 9 is an end to end plan view of the alignment of the brush proximal drive shaft end and a guidewire proximal end prior to their insertion into the distal drive motor lumen end opening.

FIG. 9 is an end-to-end plan view of the alignment of the brush proximal drive shaft end 23 and a guidewire proximal end 41 prior to their insertion into the distal drive motor lumen end opening 246. FIG. 9 also depicts the dimensional relation between the components of the proximal drive portion 29 and the mating components of the sub-assembly connector 70 and along the drive motor lumen 210. The proximal drive portion 29 is defined by the portion of the proximal drive shaft section 24 that is proximal to and includes the proximal stop 46. All of the proximal drive portion 29 is adapted to be received within the drive motor unit lumen 210.

In FIG. 9, the distal stop 44 is depicted withdrawn proximally against the proximal annular seat 82 in contrast to the position depicted in FIG. 2. This withdrawal is effected manually. The brush 26 and distal drive shaft section 22 are retracted into the brush delivery catheter lumen 32 to facilitate advancement of the brush sub-assembly 100 over the guidewire 40 to the site of the soft obstruction. The brush bristles of brush 26 are preferably formed as described in the above-referenced '(9135390.APP) application. The brush bristles are folded down "with the grain" against the distal drive shaft section 22 and the surrounding inner wall of catheter lumen 32 and extend distally as they are garaged therein.

Figure 10:
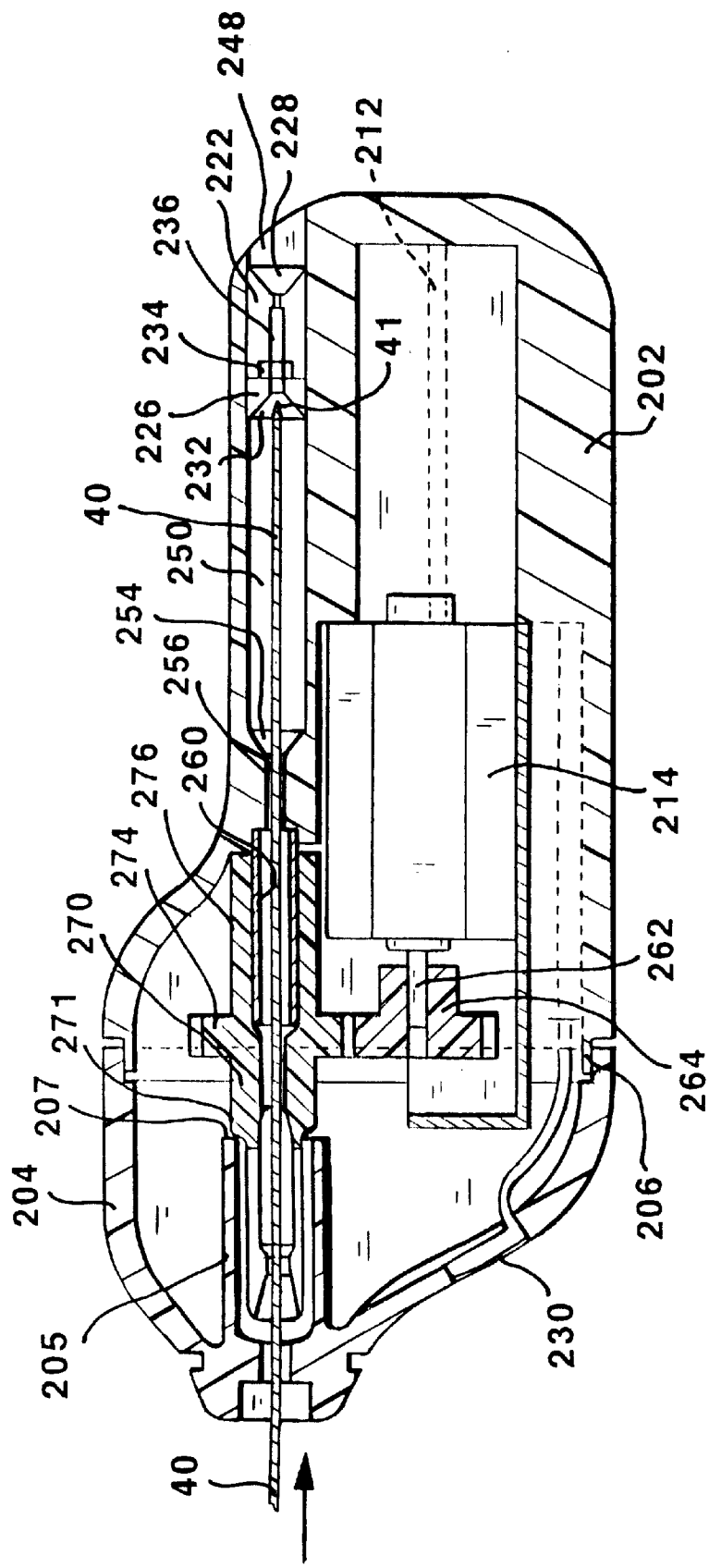
FIG. 10 is a side partial cross-section view of the drive motor unit depicting the insertion of the proximal end of the guidewire into the distal drive motor lumen end opening and its distal advancement through the drive motor lumen to exit its proximal end opening.

FIG. 10 is a side partial cross-section view of the drive motor unit 200 depicting the insertion of the guidewire proximal end 41 into the distal drive motor lumen end opening 246 and its distal advancement through the drive motor lumen 210 to exit its proximal end opening 248. The conical guide surfaces of the expandable chuck 280 and the guide funnel 232 direct and guide the proximal advancement of the guidewire proximal end 41 through the drive motor lumen 210. The brush sub-assembly 100 and the drive motor unit 200 are then positioned to be brought together by attachment of the sub-assembly connector 70 with the drive motor unit connector 239.

FIG. 11 depicts the partial proximal advancement of the brush shaft proximal drive portion 29 into the drive motor lumen 210 over the guidewire 40. The clip ends 77 and 79 of the clips 76 and 78 ride upon and are separated apart by the cam surface 242. The proximal drive shaft end 23 approach the O-ring seal 224. The four chuck elements of drive chuck 280 are spread apart at their free ends within the bore of tube 205 by the outer surface of the cylinder 92. The bar 94 is already inserted partly into the square chuck bore 286.

Figure 12:
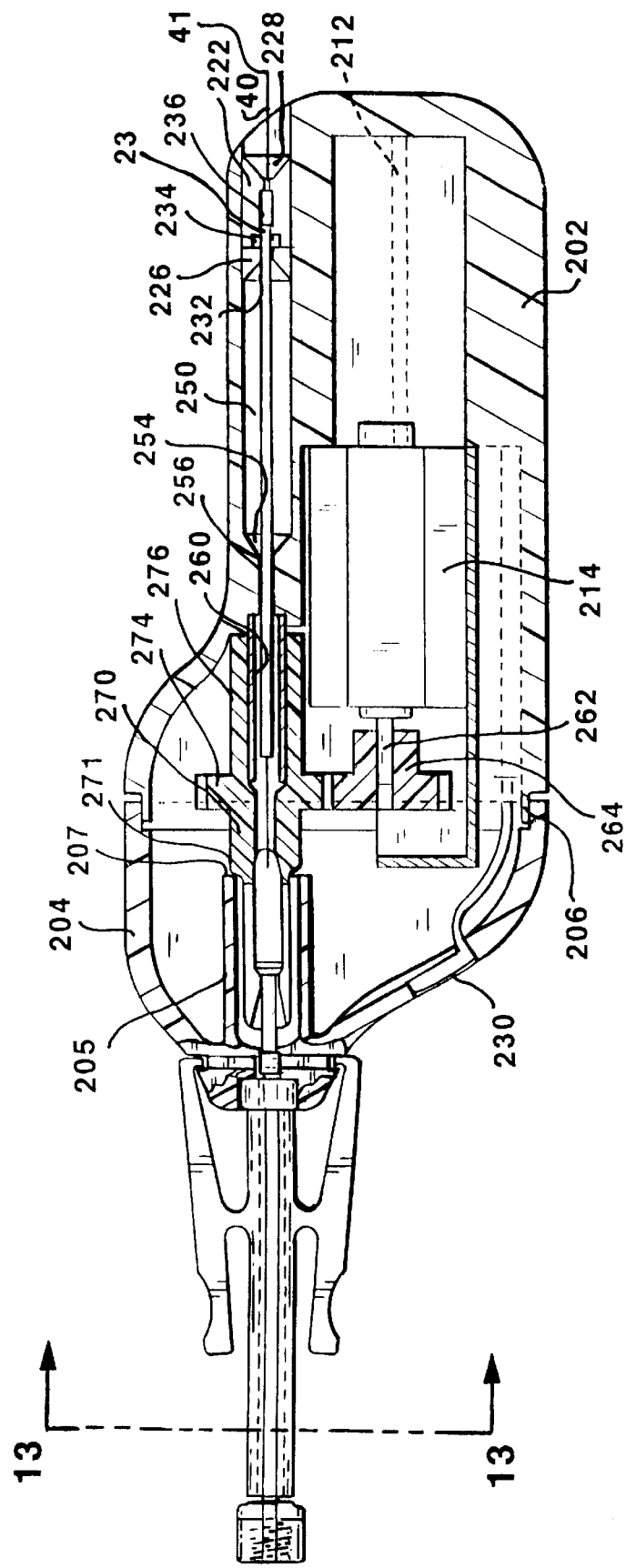
FIG. 12 is a side partial cross-section view of the drive motor unit depicting the advancement of the brush shaft proximal end into the drive motor lumen over the guidewire to the fully seated position and the engagement of the clips into the groove encircling the nose of the drive motor housing.
Figure 13:
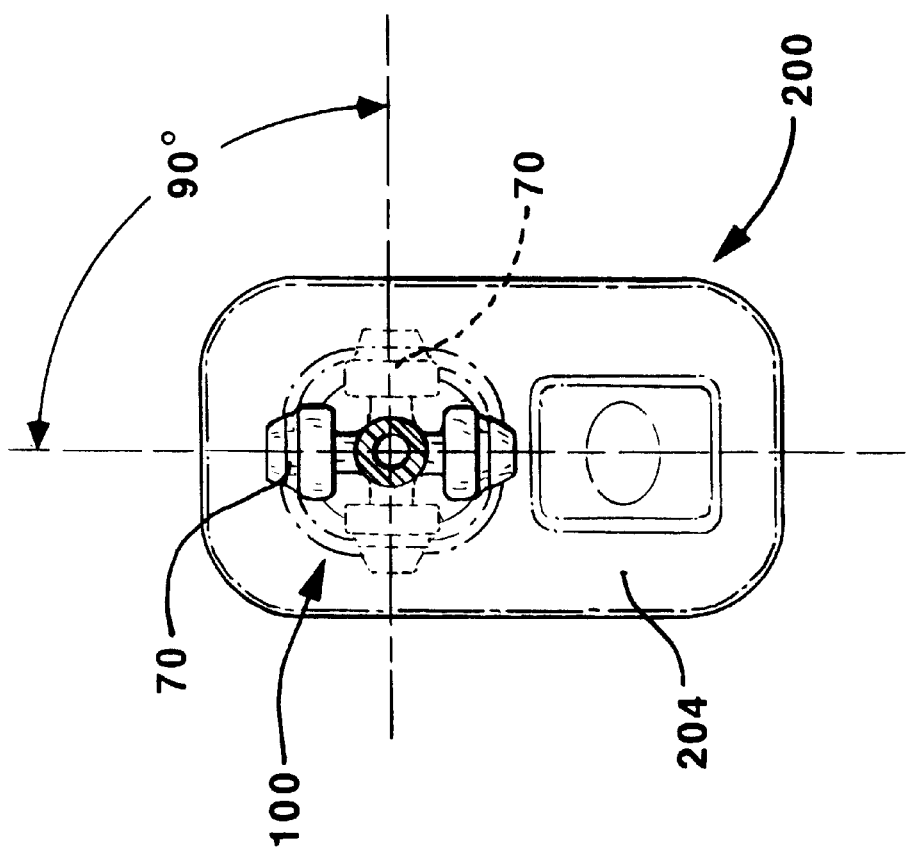
FIG. 13 is a distal end view of the drive motor unit and the clip connector taken along lines 13—13 of FIG. 12 and the rotation thereof to a further angular orientation of the brush sub-assembly with the drive motor unit.

FIG. 12 is a side partial cross-section view of the drive motor unit 200 depicting the full advancement of the proximal drive portion 29 into the drive motor lumen 210 over the guidewire 40 to the fully seated position. The clip ends 77 and 79 are dropped into the retention groove 240. FIG. 13 is a distal end view of the drive motor unit 200 and the clip connector 70 taken along lines 13—13 of FIG. 12. FIG. 13 depicts the rotation of the clip connector 70 to a further angular orientation of the brush sub-assembly 100 with respect the drive motor unit 200.

The attachment of the brush sub-assembly connector 70 with the drive motor unit connector 239 is thus effected by axially aligning the proximal seat 82 with the annular receptacle 244 and pressing the free clip ends 77 and 79 against the cam surface 242 to cause the free clip ends 77 and 79 to ride upon the cam surface 242 and to separate apart. The separation continues until the free clip ends 77 and 79 slip into the retention groove 240 and lock therein. The clip connector 70, the Y-connector 50 and the drug delivery catheter 30 can be rotated manually through 360° around the brush drive shaft 20 and the guidewire 40 as the free clip ends 77 and 79 slip along and within the retention groove 240.

The detachment of the free clip ends 77 and 79 from the retention groove 240 for removing the brush sub-assembly 100 from the drive motor unit 200 is effected by depressing the finger grips 72 and 74 toward one another and drawing the drive motor unit 200 and brush sub-assembly apart. The hinges 73 and 75 (FIG. 3) allow the finger grips 72 and 74 to be squeezed together toward the connector barrel 71 which increases the separation of the free clip ends 77 and 79 until they are released from the retention groove 240.

Summarizing the use of the motor and brush assembly 10 in a thrombolytic procedure, a percutaneous access is provided into an occluded medical implant lumen or into vasculature leading to an occluded native blood vessel or vascular implant in a conventional manner as disclosed in the above-incorporated '653 patent and Cragg Thrombolytic Brush™ literature, for example. The guidewire 40 is advanced through the access device and the vasculature or directly into the accessed medical implant until its distal end passes through the soft obstruction in the lumen thereof. The guidewire proximal end 41 extends proximally from the vasculature access device extending through the skin. Then, it is possible to advance the brush sub-assembly 100 over the guidewire 40 while the distal brush 26 is garaged within the distal section of the brush delivery catheter lumen 32 as described above with respect to FIG. 9. The advancement of the distal ends of the brush delivery catheter 30 and the drive shaft 20 can be monitored by observing the distal end radiopaque markers using fluoroscopy. When the site of the soft obstruction is reached, advancement over the guidewire 40 is halted. Typically, the brush sub-assembly is advanced over the guidewire until it is disposed distally of the soft obstruction so that it can be treated as described below in sections as the brush sub-assembly is retracted proximally through it.

After the soft obstruction is reached, the guidewire proximal end 41 is inserted into the distal drive motor lumen end opening 246 as described with reference to FIGS. 9 and 10 until the guidewire distal end 43 of the guidewire 40 extends proximally from the proximal seal assembly 220. At this point, the proximal drive shaft end 23 is inserted into the distal drive motor lumen end opening 246 and advanced as described with reference to FIGS. 11 and 12. During the approach, the clips 76 and 78 spread apart as the respective clip free ends 77 and 79 bear against and then ride up on the generally conical cam surface 242. When the clip free ends 77 and 79 snap into the annular retention groove 240, a number of operations are completed and connections are made. Simultaneously, the proximal drive shaft end 23 is seated into the proximal seal assembly 220, the enlarged shaft hub 90 is seated into the drive chuck receptacles 286 and 288, the brush 26 is advanced distally out of the distal section of the brush delivery catheter lumen 32, and the proximal stop 46 fits into the distal drive motor lumen end opening 246.

When assembly is complete as shown in FIG. 1, the brush sub-assembly 100 and the drive motor unit 200 can be rotated with respect to one another to orientations that facilitate the infusion and manual manipulation of the assembly by the physician as shown in FIG. 13. Then, the drive motor unit switch 230 is closed to energize the drive motor. The brush 26 is rotated through rotation of the drive shaft 20 by the proximal drive motor unit 200 in the prescribed rotation direction for macerating the soft obstruction. At the same time, a thrombolytic agent is applied through the side extension 62 and through the brush delivery catheter lumen 32 to the region of the brush 26. The rotation of the brush bristles causes the brush 26 to macerate the soft obstruction and to impart a rotational velocity to the fragments. In such clinical use, the brush 26 is rotated at a speed and direction that effects a pumping action in the blood that maintains the soft obstruction fragments in contact with the delivered thrombolytic agent rather than moving the mixture distally away from the brush 26.

The guidewire 40 can be left in place during rotation of the brush 26 or it can be retracted from the drive shaft lumen 28 and the proximal drive motor lumen end opening 248. The guidewire or a different guidewire, infusion wire, or a balloon or basket bearing guidewire or miniature catheter can be advanced distally into the exposed drive shaft lumen proximal end opening and out of the distal end opening thereof.

When the guidewire 40 or other elongated medical device is inserted through the drive shaft lumen 28, some amount of blood and infused thrombolytic agent leaks back through it and escapes from the drive shaft lumen proximal end opening. The blood escapes proximally to the dynamic seal assembly 220, and the dynamic seal assembly 220 prevents it from infiltrating into the interior of the drive motor unit 200. Appreciably greater amounts of blood and infused thrombolytic agent are emitted from the drive shaft lumen proximal end opening when the guidewire 40 is removed from the drive shaft lumen 28. In this case, the physician can stop the proximal drive motor lumen end opening 248 with a finger. Again, the blood pools in the opening proximally to the dynamic seal assembly 220, and the dynamic seal assembly 220 prevents it from infiltrating into the interior of the drive motor unit 200.

Figure 14:
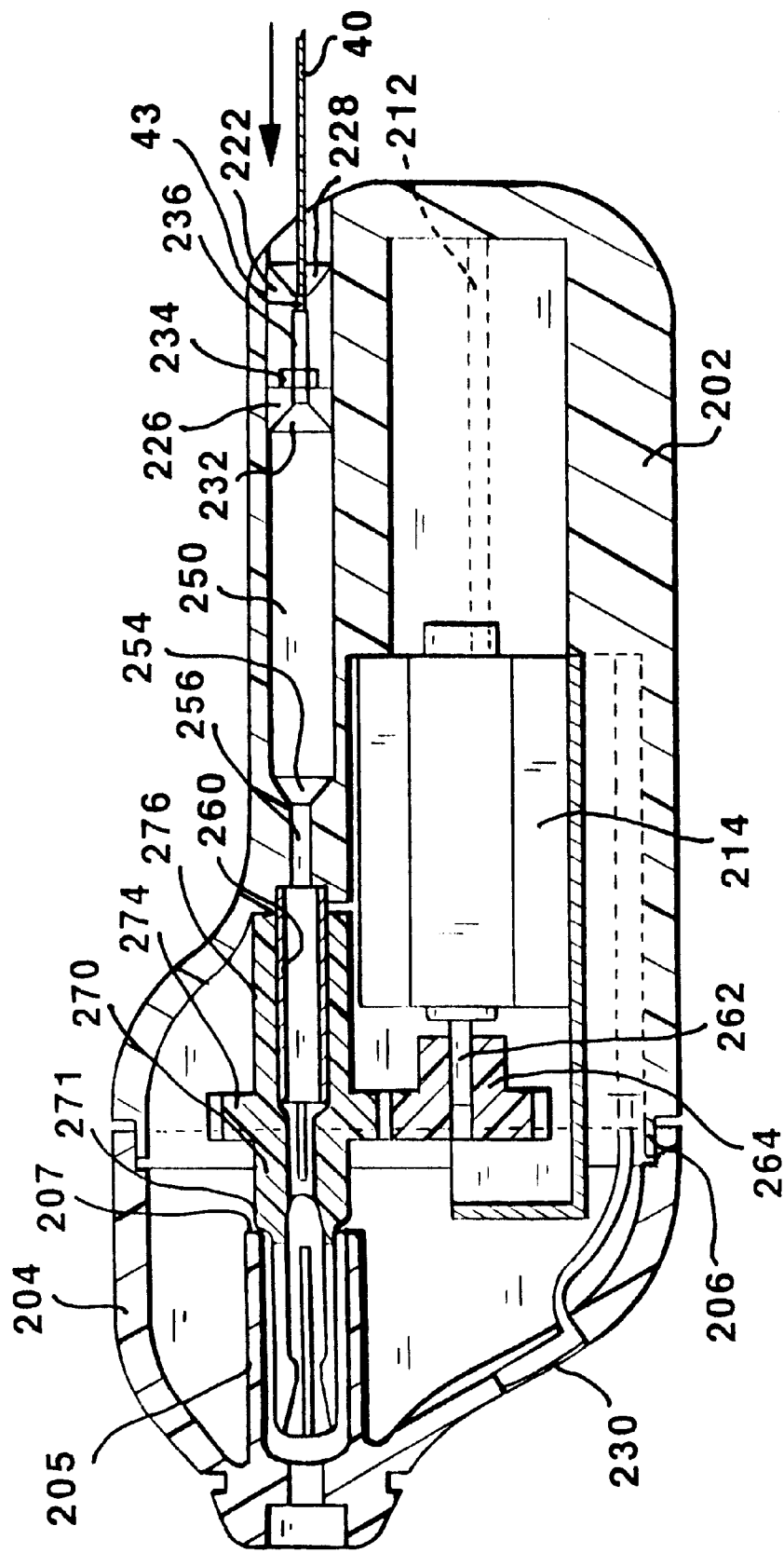
FIGS. 14 and 15 depict the insertion into the proximal end opening and distal advancement of a guidewire through the rear seal and a guide in the drive motor lumen that facilitates replacement of guidewires.
Figure 15:
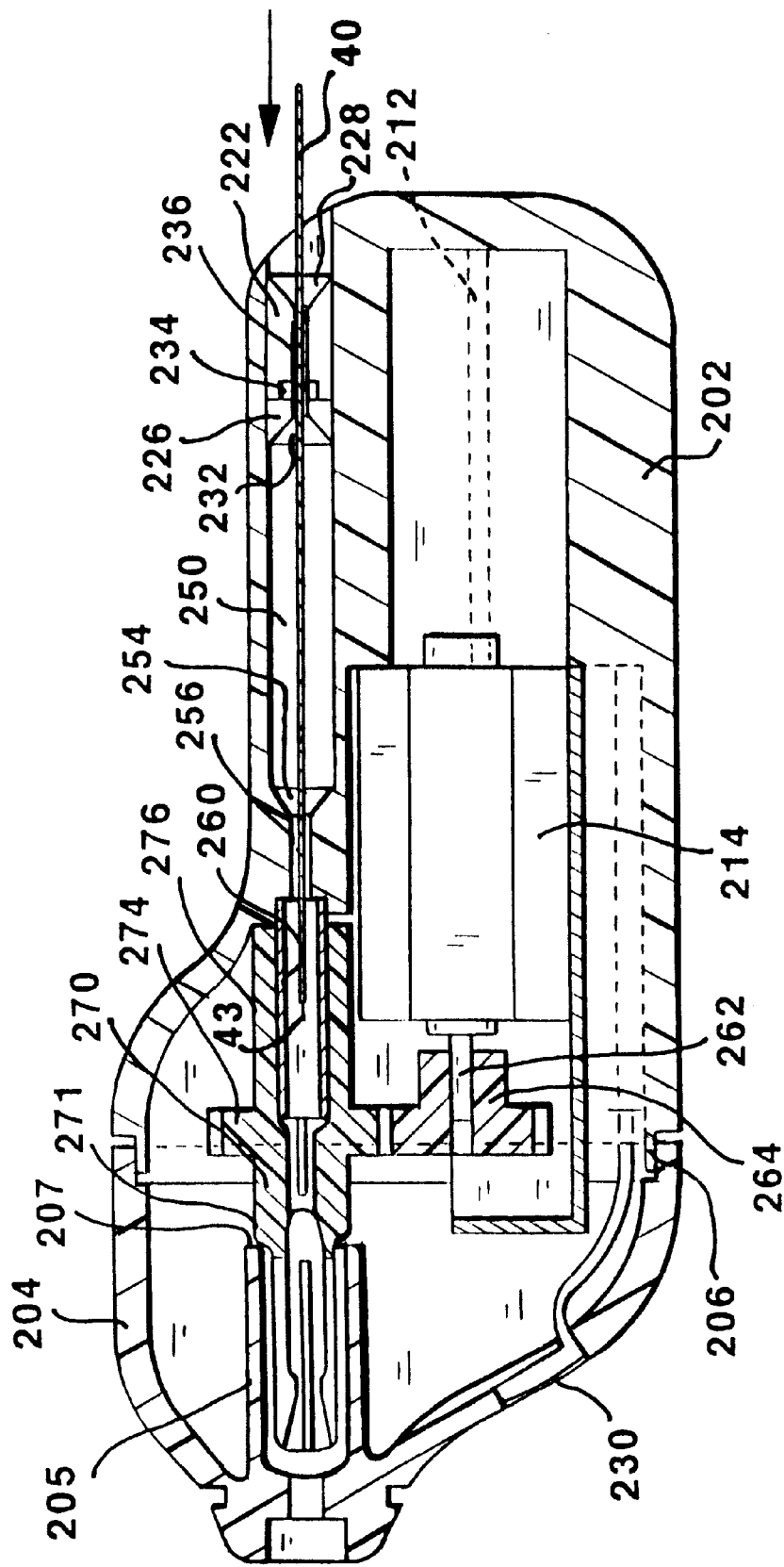

At times, it is also desirable to be able to advance a guidewire 40 distally through the drive motor lumen 210 when the proximal drive portion 91 is not seated therein. For example, during a medical thrombectomy procedure, a guidewire may be damaged and have to be replaced while the brush is kept housed within the brush delivery catheter lumen. The brush sub-assembly 100 can be disconnected from the drive motor unit 200 and the guidewire distal end 43 advanced through the drive shaft lumen 32, and the guidewire proximal end 41 can be inserted into and advanced proximally through the drive motor lumen 210. Alternatively, the guidewire distal end 43 can be advanced first through the drive motor lumen 210 and then through the drive shaft lumen 32. In either case, the brush sub-assembly 100 and the drive motor unit 200 can then be reattached after replacement and repositioning of the guidewire 40 to expel the brush from the brush delivery catheter lumen. FIGS. 14 and 15 depict the insertion of the guidewire distal end 43 into the proximal drive motor lumen end opening 248 and distal advancement of a guidewire 40 through the dynamic rear seal 220 and through distal conical guide 254 that facilitates such distal advancement of a guidewire 40.

The apparatus may be modified to allow infusate to be delivered down the drive shaft lumen 26 as disclosed in certain embodiments of the above-incorporated '653 patent. The distal drive shaft section 22 may be pre-formed with weep holes or perforations to allow the dispersion of dissolving agents or other fluids introduced down the lumen while the guidewire 40 is present or after it is withdrawn. The drive shaft lumen distal end opening may be provided with self sealing flaps to seal about the guidewire 40 while the brush is advanced or to seal the lumen end opening after the guidewire 40 is retracted. This ensures that the introduced fluid is dispersed within or proximal to the brush bristles. The drive shaft lumen distal end opening may alternatively be left open to provide a fluid dispersion or flush operation distal to the brush 26. These and other features of and methods of use of the brush described in the above-incorporated '653 and '355 patents may be employed in the use of the miniaturized brush of the present invention.

The miniaturized brush of the present invention provide reduced overall outer diameter that enables its introduction through small diameter brush delivery catheter and/or blood vessel lumens. In addition, the thin wall construction provides a drive shaft lumen 28 with a relatively enlarged inner diameter for introduction over a guidewire that may be 0.035 inches in diameter, for example, and for introduction and passage of fluids therethrough. The drive shaft 20 in each assembly is reinforced sufficiently to allow advancement through tortuous blood vessel passageways and to provide torque transfer to the distal brush 10, 10'.

In the preferred embodiment of the invention, no further apparatus is employed or steps taken to dissolve the soft obstruction or thrombus in situ. It is expected that the treatment will be commenced within hours of the onset of diagnosis, and the thrombus will be dissolved by the brushing action continually exposing the fibrin of the obstruction to the dissolving agent. To the extent that fragments are created, the agent should dissolve them before they are swept away by blood flow.

In order to contain released fragments so that the dissolving agent may complete dissolution, the brush may be introduced through the soft obstruction downstream and rotated as the brush is slowly retracted through the obstruction. Optionally, a balloon catheter or a mesh basket may be coaxially introduced through the drive shaft lumen and placed downstream to temporarily obstruct the blood and dissolving agent flow away from the site and restrain fragments to allow the concentrated dissolving agent to complete the dissolution thereof.

Advantageously, blood clots and thrombi are more readily dissolved by the mixing action of the brush bristles as the dissolving agent is introduced. Intimal hyperplasia and the risk of vessel wall rupture or pseudoneurism is decreased by use of the soft brush bristles. The speed of dissolution may be reduced to minutes, in comparison with hours for introduction of the dissolving agent alone. The reduced amount of dissolving agent introduced decreases the risk of internal bleeding. Patient comfort is increased and cost of the intensive care treatment is reduced by the shortened time and reduction of exposure to the dissolving agent.

While the invention is preferably used in the above-described medical procedures, it will be recognized that a miniaturized, hollow lumen brush may have other important medical applications. For example, the disclosed assembly may be employed for specimen collection from various body lumens including blood vessels and other vessels, openings, cavities or ducts, in the manner of a cytology brush.

Moreover, while the present invention is described as particularly usable and implemented in the above described Cragg Thrombolytic Brush™, it will be recognized that it can also be employed in other motor driven catheter applications employing other rotated obstruction treatment devices. For example, the obstruction treatment device of the following claims preferably constitutes the above-described flexible brush for macerating soft obstructions. However, the obstruction treatment device can take other forms proposed for removing such soft obstructions or hard obstructions of a body vessel or vascular implant or other lumen that are rotated by a drive motor unit. Such obstruction treatment devices include expandable in situ or fixed diameter wire coils or baskets of the types shown, for example, in U.S. Pat. Nos. 4,646,736, 5,195,954 and 5,330,484, incorporated herein by reference. The obstruction treatment device can also take the form of a cutting mechanism, e.g., an atherectomy cutting head of one of the many known types, e.g. the cutting screw shown in U.S. Pat. No. 5,423,799 or the expandable wires or blades shown in U.S. Pat. No. 5,030,201, both incorporated herein by reference.

Although the preferred embodiments of the invention described above are used with hollow drive shaft 20, it will be understood that the same connector techniques may be used to connect brush and obstruction treatment device sub-assemblies having solid core, rotatable brush drive shafts with drive motor units.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

We claim:

1. A motor and brush assembly preferably for use in a medical procedure at a site within a patient's body comprising:

a brush sub-assembly comprising:
an elongated, flexible, rotatable brush drive shaft extending between a proximal drive shaft end and a distal drive shaft end and formed with a drive shaft lumen extending between drive shaft lumen proximal and distal end openings at the proximal and distal drive shaft ends;
a brush formed in a distal portion of the brush drive shaft;
a proximal drive member formed in a proximal portion of said brush drive shaft a brush sub-assembly connector comprising a brush sub-assembly connector;
an elongated, flexible, brush delivery catheter extending between a proximal catheter end and a distal catheter end and formed with a catheter lumen extending between proximal and distal catheter lumen end openings at the proximal and distal catheter ends, and
means for fitting a distal drive shaft section of said brush drive shaft within said catheter lumen and for extending said proximal drive member proximally of said proximal catheter lumen end opening for allowing rotation of said brush drive shaft with respect to said brush delivery catheter; and a drive motor unit adapted to be coupled with said brush sub-assembly to effect rotation of said brush drive shaft further comprising:
a drive motor housing containing a drive motor lumen extending between drive motor lumen proximal and distal end openings in said drive motor housing, said drive motor lumen dimensioned to receive said proximal drive member;
drive means located within said drive motor housing for engaging said proximal drive member when it is inserted through said distal drive motor lumen end opening and into said drive motor lumen and for rotating said drive shaft; and seal means located along said drive motor lumen adjacent to the proximal drive motor lumen end opening for engaging said proximal drive shaft end and operable to prevent infiltration of fluids at the site that backflow into the drive shaft lumen distal end opening when said distal drive shaft end is positioned at the site through the drive shaft lumen and out of the drive shaft lumen proximal end opening and into the drive motor housing, said drive means further comprising a drive motor unit connector for positively engaging said brush sub-assembly connector as said proximal drive member is inserted through said drive motor lumen distal end opening and said proximal drive shaft end is engaged by said seal means.

2. The assembly of claim 1, wherein:

said drive shaft lumen is dimensioned to receive guidewires and other elongated medical devices; and said drive motor lumen is dimensioned to receive said proximal drive member to locate said proximal drive shaft end in alignment with said proximal drive motor lumen end opening and within said seal means while keeping the drive shaft lumen proximal end open and accessible to allow insertion of guidewires and other medical devices therethrough and into said drive shaft lumen when said brush sub-assembly and said drive motor unit are coupled together.

3. The assembly of claim 1, wherein said brush sub-assembly further comprises means for providing limited axial movement of said brush drive shaft with respect to said brush delivery catheter and said fitting means for allowing retraction of said drive shaft proximally a predetermined distance sufficient to retract said brush proximally into said brush delivery catheter to facilitate introduction and passage of the brush sub-assembly to the site in the patient's body and for allowing extension of said drive shaft distally through the predetermined distance at the site when the proximal drive member is received and seated in the drive motor lumen.

4. The assembly of claim 1, wherein the site in the patient's body is a site of a soft obstruction of a blood vessel of the patient's vascular system, and wherein:

said brush sub-assembly further comprises means for providing limited axial movement of said brush drive shaft with respect to said brush delivery catheter and said fitting means for allowing retraction of said drive shaft proximally a predetermined distance sufficient to retract said brush proximally into said brush delivery catheter to facilitate introduction and passage of the brush sub-assembly through a patient's vascular system to the site of a soft obstruction and for allowing extension of said drive shaft distally through the predetermined distance at the site of the soft obstruction when the proximal drive member is received and seated in the drive motor lumen.

5. The assembly of claim 1, wherein said drive motor lumen further comprises distal guide means operable when the proximal drive shaft end is inserted through said distal drive motor lumen end opening and advanced proximally for directing the insertion of the proximal drive shaft end into engagement with said sealing means.

6. The assembly of claim 1, further comprising:

an elongated guidewire having a proximal guidewire end and a distal guidewire end adapted to be inserted into the patient's body to the site, and wherein:

said drive shaft lumen is dimensioned to receive said guidewire introduced through said drive shaft lumen proximal and distal end openings; and said drive motor lumen further comprises distal guide means for enabling the proximal advancement of a guidewire proximal end extending proximally from said drive shaft lumen proximal end opening through said distal drive motor lumen end opening, said drive motor lumen, said sealing means and from said proximal drive motor lumen end opening to thereby locate said guidewire proximal end proximally to said drive motor unit before the proximal drive member is advanced through said distal drive motor lumen end opening and seated in said drive shaft lumen.

7. The assembly of claim 6, wherein said distal guide means are further operable when the proximal drive shaft end is inserted through said distal drive motor lumen end opening and advanced proximally over the guidewire extending therethrough for directing the insertion of the proximal drive shaft end into engagement with said sealing means.

8. The assembly of claim 7, wherein said distal guide means comprises a further funnel shaped guide located within said drive motor lumen distally to said seal means for directing said proximal guidewire end into said seal means during proximal advancement of said guidewire.

9. The assembly of claim 6, wherein said distal guide means comprises a further funnel shaped guide located within said drive motor lumen distally to said seal means for directing said proximal guidewire end into said seal means during proximal advancement of said guidewire.

10. The assembly of claim 1, further comprising:

an elongated medical device having a proximal device end and a distal device end, and wherein:

said drive shaft lumen is dimensioned to receive said elongated medical device introduced through said and drive shaft lumen proximal and distal end openings; and said drive motor lumen further comprises proximal guide means for enabling the distal advancement of said distal device end through said proximal drive motor lumen end opening into said drive motor lumen and distally through said sealing means and from said distal drive motor lumen end opening to thereby locate said device distal end distally to said drive motor unit to enable advancement of the proximal drive member through said distal drive motor lumen end opening and over the elongated medical device extending through the drive motor lumen until the proximal drive member is seated in said drive shaft lumen.

11. The assembly of claim 10, wherein said proximal guide means comprises a funnel shaped guide located at said proximal drive motor lumen end opening proximally to said seal means for directing said distal device end into said seal means during distal advancement of said elongated medical device.

12. The assembly of claim 10, wherein said elongated medical device is a guidewire.

13. The assembly of claim 1, wherein said fitting means of said brush sub-assembly further comprises means for introducing a diagnostic or therapeutic agent into said brush delivery catheter lumen for transmission through said catheter lumen alongside said distal drive shaft section within said catheter lumen and emission from said catheter lumen distal end opening.

14. A motor and brush assembly preferably for use in a medical procedure at a site within a patient's body comprising:

an elongated guidewire having a proximal guidewire end and a distal guidewire end adapted to be inserted into the patient's body to the site;

a brush sub-assembly comprising:

an elongated, flexible, rotatable brush drive shaft extending between a proximal drive shaft end and a distal drive shaft end and formed with a drive shaft lumen extending between drive shaft lumen proximal and distal end openings at the proximal and distal drive shaft ends, said drive shaft lumen dimensioned to receive said guidewire introduced through said drive shaft lumen proximal and distal end openings;

a brush formed in a distal portion of the brush drive shaft;

a proximal drive member formed in a proximal portion of said brush drive shaft comprising a brush sub-assembly connector;

an elongated, flexible, brush delivery catheter extending between a proximal catheter end and a distal catheter end and formed with a catheter lumen extending between proximal and distal catheter lumen end openings at the proximal and distal catheter ends, and means for fitting a distal drive shaft section of said brush drive shaft within said catheter lumen and for extending said proximal drive member proximally of said proximal catheter lumen end opening for allowing rotation of said brush drive shaft with respect to said brush delivery catheter; and a drive motor unit adapted to be coupled with said brush sub-assembly to effect rotation of said brush drive shaft further comprising:

a drive motor housing containing a drive motor lumen extending between drive motor lumen proximal and distal end openings in said drive motor housing, said drive motor lumen dimensioned to receive said proximal drive member;

drive means located within said drive motor housing for engaging said proximal drive member when it is inserted through said distal drive motor lumen end opening and into said drive motor lumen and for rotating said drive shaft; and distal guide means for enabling the proximal advancement of said guidewire proximal end through said distal drive motor lumen end opening and said drive motor lumen and from said proximal drive motor lumen end opening to thereby locate said guidewire proximal end proximally to said drive motor unit before the proximal drive member is advanced over said guidewire through said distal drive motor lumen end opening and seated in said drive shaft lumen, said drive means further comprising a drive motor unit connector for positively engaging said brush sub-assembly connector as said proximal drive member is inserted through said drive motor lumen distal end opening and said proximal drive shaft end is engaged by said seal means.

15. The assembly of claim 14, wherein said distal guide means are further operable when the proximal drive shaft end is inserted through said distal drive motor lumen end opening and advanced proximally over the guidewire extending therethrough for directing the insertion of the proximal drive shaft end through said drive motor lumen.

16. The assembly of claim 14, wherein said drive motor lumen further comprises proximal guide means for enabling the distal advancement of said guidewire distal end through said proximal drive motor lumen end opening and distally through said drive motor lumen and from said distal drive motor lumen end opening to thereby locate said guidewire distal end distally to said drive motor unit to enable advancement of the proximal drive member through said distal drive motor lumen end opening and over the guidewire extending through the drive motor lumen until the proximal drive member is seated in said drive shaft lumen.

17. The assembly of claim 16, wherein said proximal guide means comprises a funnel shaped guide located at said proximal drive motor lumen end opening proximally to said seal means for directing said distal device end into said seal means during distal advancement of said elongated medical device.

18. The assembly of claim 14, wherein said distal guide means are further operable when the proximal drive shaft end is inserted through said distal drive motor lumen end opening and advanced proximally over the guidewire extending therethrough for directing the insertion of the proximal drive shaft end through said drive motor lumen.

19. The assembly of claim 14, wherein said distal guide means comprises a further funnel shaped guide located within said drive motor lumen distally to said seal means for directing said proximal guidewire end into said seal means during proximal advancement of said guidewire.

20. The assembly of claim 14, wherein said fitting means of said brush sub-assembly further comprises means for introducing a diagnostic or therapeutic agent into said brush delivery catheter lumen for transmission through said catheter lumen alongside said distal drive shaft section within said catheter lumen and emission from said catheter lumen distal end opening.

21. The assembly of claim 14, wherein said distal guide means are further operable when the proximal drive shaft end is inserted through said distal drive motor lumen end opening and advanced proximally over the guidewire extending therethrough for directing the insertion of the proximal drive shaft end through said drive motor lumen.

22. A motor and brush assembly preferably for use in a medical procedure at a site within a patient's body comprising:

a brush sub-assembly comprising:

an elongated, flexible, rotatable brush drive shaft extending between a proximal drive shaft end and a distal drive shaft end;

a brush formed in a distal portion of the brush drive shaft;

a proximal drive member formed in a proximal portion of said brush drive shaft;

an elongated, flexible, brush delivery catheter extending between a proximal catheter end and a distal catheter end and formed with a catheter lumen extending between proximal and distal catheter lumen end openings at the proximal and distal catheter ends, and means for fitting a distal drive shaft section of said brush drive shaft within said catheter lumen and for extending said proximal drive member proximally of said proximal catheter lumen end opening for allowing rotation of said brush drive shaft with respect to said brush delivery catheter; and a drive motor unit adapted to be coupled with said brush sub-assembly to effect rotation of said brush drive shaft further comprising:

a drive motor housing containing a drive motor lumen extending between drive motor lumen proximal and distal end openings in said drive motor housing, said drive motor lumen dimensioned to receive said proximal drive member;

drive means located within said drive motor housing for engaging said proximal drive member when it is inserted through said distal drive motor lumen end opening and into said drive motor lumen and for rotating said drive shaft; and distal guide means for enabling the proximal advancement of said proximal drive member through said distal drive motor lumen end opening and said drive motor lumen and from said proximal drive motor lumen end opening to thereby locate said proximal drive shaft end proximally to said drive motor unit when the proximal drive member is advanced through said distal drive motor lumen end opening and seated in said drive shaft lumen.

23. The assembly of claim 22, wherein said drive shaft is formed with a drive shaft lumen extending between drive shaft lumen proximal and distal end openings at the proximal and distal drive shaft ends, and said drive shaft lumen is dimensioned to receive an elongated medical device introduced through said drive shaft lumen proximal and distal end openings.

24. A motor and obstruction treatment device assembly preferably for use in a medical procedure at a site within a patient's body comprising:

an obstruction treatment device sub-assembly comprising:

an elongated, flexible, rotatable obstruction treatment device drive shaft extending between a proximal drive shaft end and a distal drive shaft end and formed with a drive shaft lumen extending between drive shaft lumen proximal and distal end openings at the proximal and distal drive shaft ends;

an obstruction treatment device formed in a distal portion of the obstruction treatment device drive shaft;

a proximal drive member formed in a proximal portion of said obstruction treatment device drive shaft comprising an obstruction treatment sub-assembly connector;

an elongated, flexible, obstruction treatment device delivery catheter extending between a proximal catheter end and a distal catheter end and formed with a catheter lumen extending between proximal and distal catheter lumen end openings at the proximal and distal catheter ends, and means for fitting a distal drive shaft section of said obstruction treatment device drive shaft within said catheter lumen and for extending said proximal drive member proximally of said proximal catheter lumen end opening for allowing rotation of said obstruction treatment device drive shaft with respect to said obstruction treatment device delivery catheter; and a drive motor unit adapted to be coupled with said obstruction treatment device sub-assembly to effect rotation of said obstruction treatment device drive shaft further comprising:

a drive motor housing containing a drive motor lumen extending between drive motor lumen proximal and distal end openings in said drive motor housing, said drive motor lumen dimensioned to receive said proximal drive member;

drive means located within said drive motor housing for engaging said proximal drive member when it is inserted through said distal drive motor lumen end opening and into said drive motor lumen and for rotating said drive shaft; and seal means located along said drive motor lumen adjacent to the proximal drive motor lumen end opening for engaging said proximal drive shaft end and operable to prevent infiltration of fluids at the site that backflow into the drive shaft lumen distal end opening when said distal drive shaft end is positioned at the site through the drive shaft lumen and out of the drive shaft lumen proximal end opening and into the drive motor housing, said drive means further comprising a drive motor unit connector for positively engaging said obstruction treatment sub-assembly connector as said proximal drive member is inserted through said drive motor lumen distal end openings and said proximal drive shaft end is engaged by said seal means.

25. The assembly of claim 24, wherein:

said drive shaft lumen is dimensioned to receive guidewires and other elongated medical devices; and said drive motor lumen is dimensioned to receive said proximal drive member to locate said proximal drive shaft end in alignment with said proximal drive motor lumen end opening and within said seal means while keeping the drive shaft lumen proximal end open and accessible to allow insertion of guidewires and other medical devices therethrough and into said drive shaft lumen when said obstruction treatment device sub-assembly and said drive motor unit are coupled together.

26. The assembly of claim 24, wherein said obstruction treatment device sub-assembly further comprises means for providing limited axial movement of said obstruction treatment device drive shaft with respect to said obstruction treatment device delivery catheter and said fitting means for allowing retraction of said drive shaft proximally a predetermined distance sufficient to retract said obstruction treatment device proximally into said obstruction treatment device delivery catheter to facilitate introduction and passage of the obstruction treatment device sub-assembly to the site in the patient's body and for allowing extension of said drive shaft distally through the predetermined distance at the site when the proximal drive member is received and seated in the drive motor lumen.

27. The assembly of claim 24, wherein the site in the patient's body is a site of a soft obstruction of a blood vessel of the patient's vascular system, and wherein:

said obstruction treatment device sub-assembly further comprises means for providing limited axial movement of said obstruction treatment device drive shaft with respect to said obstruction treatment device delivery catheter and said fitting means for allowing retraction of said drive shaft proximally a predetermined distance sufficient to retract said obstruction treatment device proximally into said obstruction treatment device delivery catheter to facilitate introduction and passage of the obstruction treatment device sub-assembly through a patient's vascular system to the site of a soft obstruction and for allowing extension of said drive shaft distally through the predetermined distance at the site of the soft obstruction when the proximal drive member is received and seated in the drive motor lumen.

28. The assembly of claim 24, wherein said drive motor lumen further comprises distal guide means operable when the proximal drive shaft end is inserted through said distal drive motor lumen end opening and advanced proximally for directing the insertion of the proximal drive shaft end into engagement with said sealing means.

29. The assembly of claim 24, further comprising:

an elongated guidewire having a proximal guidewire end and a distal guidewire end adapted to be inserted into the patient's body to the site, and wherein:

said drive shaft lumen is dimensioned to receive said guidewire introduced through said drive shaft lumen proximal and distal end openings; and said drive motor lumen further comprises distal guide means for enabling the proximal advancement of a guidewire proximal end extending proximally from said drive shaft lumen proximal end opening through said distal drive motor lumen end opening, said drive motor lumen, said sealing means and from said proximal drive motor lumen end opening to thereby locate said guidewire proximal end proximally to said drive motor unit before the proximal drive member is advanced through said distal drive motor lumen end opening and seated in said drive shaft lumen.

30. The assembly of claim 29, wherein said distal guide means are further operable when the proximal drive shaft end is inserted through said distal drive motor lumen end opening and advanced proximally over the guidewire extending therethrough for directing the insertion of the proximal drive shaft end into engagement with said sealing means.

31. The assembly of claim 30, wherein said distal guide means comprises a further funnel shaped guide located within said drive motor lumen distally to said seal means for directing said proximal guidewire end into said seal means during proximal advancement of said guidewire.

32. The assembly of claim 29, wherein said distal guide means comprises a further funnel shaped guide located within said drive motor lumen distally to said seal means for directing said proximal guidewire end into said seal means during proximal advancement of said guidewire.

33. The assembly of claim 24, further comprising:

an elongated medical device having a proximal device end and a distal device end, and wherein:

said drive shaft lumen is dimensioned to receive said elongated medical device introduced through said and drive shaft lumen proximal and distal end openings; and said drive motor lumen further comprises proximal guide means for enabling the distal advancement of said distal device end through said proximal drive motor lumen end opening into said drive motor lumen and distally through said sealing means and from said distal drive motor lumen end opening to thereby locate said device distal end distally to said drive motor unit to enable advancement of the proximal drive member through said distal drive motor lumen end opening and over the elongated medical device extending through the drive motor lumen until the proximal drive member is seated in said drive shaft lumen.

34. The assembly of claim 33, wherein said proximal guide means comprises a funnel shaped guide located at said proximal drive motor lumen end opening proximally to said seal means for directing said distal device end into said seal means during distal advancement of said elongated medical device.

35. The assembly of claim 33, wherein said elongated medical device is a guidewire.

36. The assembly of claim 24, wherein said fitting means of said obstruction treatment device sub-assembly further comprises means for introducing a diagnostic or therapeutic agent into said obstruction treatment device delivery catheter lumen for transmission through said catheter lumen alongside said distal drive shaft section within said catheter lumen and emission from said catheter lumen distal end opening.

37. A motor and obstruction treatment device assembly preferably for use in a medical procedure at a site within a patient's body comprising:

an elongated guidewire having a proximal guidewire end and a distal guidewire end adapted to be inserted into the patient's body to the site;

an obstruction treatment device sub-assembly comprising:

an elongated, flexible, rotatable obstruction treatment device drive shaft extending between a proximal drive shaft end and a distal drive shaft end and formed with a drive shaft lumen extending between drive shaft lumen proximal and distal end openings at the proximal and distal drive shaft ends, said drive shaft lumen dimensioned to receive said guidewire introduced through said drive shaft lumen proximal and distal end openings;

an obstruction treatment device formed in a distal portion of the obstruction treatment device drive shaft;

a proximal drive member formed in a proximal portion of said obstruction treatment device drive shaft comprising an obstruction treatment sub-assembly connector;

an elongated, flexible, obstruction treatment device delivery catheter extending between a proximal catheter end and a distal catheter end and formed with a catheter lumen extending between proximal and distal catheter lumen end openings at the proximal and distal catheter ends, and means for fitting a distal drive shaft section of said obstruction treatment device drive shaft within said catheter lumen and for extending said proximal drive member proximally of said proximal catheter lumen end opening for allowing rotation of said obstruction treatment device drive shaft with respect to said obstruction treatment device delivery catheter; and a drive motor unit adapted to be coupled with said obstruction treatment device sub-assembly to effect rotation of said obstruction treatment device drive shaft further comprising:

a drive motor housing containing a drive motor lumen extending between drive motor lumen proximal and distal end openings in said drive motor housing, said drive motor lumen dimensioned to receive said proximal drive member;

drive means located within said drive motor housing for engaging said proximal drive member when it is inserted through said distal drive motor lumen end opening and into said drive motor lumen and for rotating said drive shaft; and distal guide means for enabling the proximal advancement of said guidewire proximal end through said distal drive motor lumen end opening and said drive motor lumen and from said proximal drive motor lumen end opening to thereby locate said guidewire proximal end proximally to said drive motor unit before the proximal drive member is advanced over said guidewire through said distal drive motor lumen end opening and seated in said drive shaft lumen, said drive means further comprising a drive motor unit connector for positively engaging said obstruction treatment sub-assembly connector as said proximal drive member is inserted through said drive motor lumen distal end opening and said proximal drive shaft end is engaged by said seal means.

38. The assembly of claim 37, wherein said drive motor lumen further comprises proximal guide means for enabling the distal advancement of said guidewire distal end through said proximal drive motor lumen end opening and distally through said drive motor lumen and from said distal drive motor lumen end opening to thereby locate said guidewire distal end distally to said drive motor unit to enable advancement of the proximal drive member through said distal drive motor lumen end opening and over the guidewire extending through the drive motor lumen until the proximal drive member is seated in said drive shaft lumen.

39. The assembly of claim 38, wherein said proximal guide means comprises a funnel shaped guide located at said proximal drive motor lumen end opening proximally to said seal means for directing said distal device end into said seal means during distal advancement of said elongated medical device.

40. The assembly of claim 37, wherein said distal guide means are further operable when the proximal drive shaft end is inserted through said distal drive motor lumen end opening and advanced proximally over the guidewire extending therethrough for directing the insertion of the proximal drive shaft end through said drive motor lumen.

41. The assembly of claim 37, wherein said distal guide means comprises a further funnel shaped guide located within said drive motor lumen distally to said seal means for directing said proximal guidewire end into said seal means during proximal advancement of said guidewire.

42. A motor and obstruction treatment device assembly preferably for use in a medical procedure at a site within a patient's body comprising:

an obstruction treatment device sub-assembly comprising:
an elongated, flexible, rotatable obstruction treatment device drive shaft extending between a proximal drive shaft end and a distal drive shaft end;
an obstruction treatment device formed in a distal portion of the obstruction treatment device drive shaft;
a proximal drive member formed in a proximal portion of said obstruction treatment device drive shaft comprising an obstruction treatment sub-assembly connector;
an elongated, flexible, obstruction treatment device delivery catheter extending between a proximal catheter end and a distal catheter end and formed with a catheter lumen extending between proximal and distal catheter lumen end openings at the proximal and distal catheter ends, and
means for fitting a distal drive shaft section of said obstruction treatment device drive shaft within said catheter lumen and for extending said proximal drive member proximally of said proximal catheter lumen end opening for allowing rotation of said obstruction treatment device drive shaft with respect to said obstruction treatment device delivery catheter; and a drive motor unit adapted to be coupled with said obstruction treatment device sub-assembly to effect rotation of said obstruction treatment device drive shaft further comprising:
a drive motor housing containing a drive motor lumen extending between drive motor lumen proximal and distal end openings in said drive motor housing, said drive motor lumen dimensioned to receive said proximal drive member;
drive means located within said drive motor housing for engaging said proximal drive member when it is inserted through said distal drive motor lumen end opening and into said drive motor lumen and for rotating said drive shaft; and
distal guide means for enabling the proximal advancement of said proximal drive member through said distal drive motor lumen end opening and said drive motor lumen and from said proximal drive motor lumen end opening to thereby locate said proximal drive shaft end proximally to said drive motor unit when the proximal drive member is advanced through said distal drive motor lumen end opening and seated in said drive shaft lumen, said drive means further comprising a drive motor unit connector for positively engaging said obstruction treatment sub-assembly connector as said proximal drive member is inserted through said drive motor lumen distal end opening and said proximal drive shaft end is engaged by said seal means.

43. The assembly of claim 42, wherein said drive shaft is formed with a drive shaft lumen extending between drive shaft lumen proximal and distal end openings at the proximal and distal drive shaft ends, and said drive shaft lumen is dimensioned to receive an elongated medical device introduced through said drive shaft lumen proximal and distal end openings.

* * * * *